(12) United States Patent
Yoshida et al.

(10) Patent No.: US 10,556,944 B2
(45) Date of Patent: Feb. 11, 2020

(54) FAB REGION-BINDING PEPTIDE

(71) Applicant: KANEKA CORPORATION, Osaka (JP)

(72) Inventors: Shinichi Yoshida, Hyogo (JP); Dai Murata, Hyogo (JP)

(73) Assignee: KANEKA CORPORATION, Osaka (JP)

( * ) Notice: Subject to any disclaimer, the term of this patent is extended or adjusted under 35 U.S.C. 154(b) by 374 days.

(21) Appl. No.: 14/914,439

(22) PCT Filed: Aug. 28, 2014

(86) PCT No.: PCT/JP2014/072524
§ 371 (c)(1),
(2) Date: Feb. 25, 2016

(87) PCT Pub. No.: WO2015/030094
PCT Pub. Date: Mar. 5, 2015

(65) Prior Publication Data
US 2016/0289306 A1   Oct. 6, 2016

(30) Foreign Application Priority Data
Aug. 30, 2013   (JP) ................................ 2013-180249

(51) Int. Cl.
*C07K 16/12*   (2006.01)
*C07K 14/315*   (2006.01)
*C07K 1/22*   (2006.01)

(52) U.S. Cl.
CPC ............ *C07K 16/1275* (2013.01); *C07K 1/22* (2013.01); *C07K 14/315* (2013.01); *C07K 2317/55* (2013.01); *C12N 2510/02* (2013.01)

(58) Field of Classification Search
None
See application file for complete search history.

(56) References Cited

U.S. PATENT DOCUMENTS

| | | | |
|---|---|---|---|
| 4,954,618 A | 9/1990 | Fahnestock | |
| 4,956,296 A | 9/1990 | Fahnestock | |
| 4,977,247 A | 12/1990 | Fahnestock et al. | |
| 5,082,773 A | 1/1992 | Fahnestock | |
| 5,229,492 A | 7/1993 | Fahnestock | |
| 5,312,901 A | 5/1994 | Fahnestock | |
| 6,133,431 A | 10/2000 | Yasuda et al. | |
| 6,663,862 B1 | 12/2003 | Hellinga et al. | |
| 2004/0038378 A1 | 2/2004 | Hellinga et al. | |
| 2006/0134805 A1 | 6/2006 | Berg et al. | |
| 2009/0299035 A1 | 12/2009 | Iwakura et al. | |
| 2016/0289306 A1 | 10/2016 | Yoshida et al. | |

FOREIGN PATENT DOCUMENTS

| | | | |
|---|---|---|---|
| JP | 63-503032 | 11/1988 | |
| JP | 3-1211400 | 5/1991 | |
| JP | 2008-115151 | 5/2008 | |
| JP | 2008-523140 | 7/2008 | |
| JP | 2009-195184 | 9/2009 | |
| JP | 2011-232098 | 11/2011 | |
| WO | 97/26930 | 7/1997 | |
| WO | 98/01560 | 1/1998 | |
| WO | 00/74728 | 12/2000 | |
| WO | WO-2007019376 A2 * | 2/2007 | ............ A61K 9/085 |
| WO | 2013/018880 | 2/2013 | |
| WO | 2013/041730 | 3/2013 | |
| WO | 2015-030094 | 3/2015 | |

OTHER PUBLICATIONS

Written Opinion of the International Searching Authority for PCT/JP2014/072524, dated Nov. 25, 2014, pp. 1-6 (Year: 2014).*
Lian et al., "Mapping the interactions between streptococcal protein G and the Fab fragment of IgG in solution", Structural Biology, 1994, vol. 1, No. 6, pp. 355-357.
Extended European Search Report dated Jun. 12, 2017 in European Patent Application No. 14841163.0.
Hober et al., "Protein A chromatography for antibody purification", Journal of Chromatography B, 2007, vol. 848, pp. 40-47.
Shukla et al., "Recent advances in large-scale production of monoclonal antibodies and related proteins", Trends Biotechnol., 2010, vol. 28, pp. 253-261.
Nelson et al., "Development trends for therapeutic antibody fragments", Nat. Biotechnol., 2009, vol. 27, pp. 331-337.
Jean-Pierre Bouvet, "Immunoglobulin Fab Fragment-Binding Proteins", Int. J. Immunopharmac, 1994, vol. 16, No. 5/6, pp. 419-424.
Derrick et al., "Crystal structure of a streptococcal protein G domain bound to an Fab fragment", Nature, 1992, vol. 359, pp. 752-754.
Lucas J. Bailey et al., "Applications for an engineered Protein-G variant with a pH controllable affinity to antibody fragments", Journal of Immunological Methods, 2014, vol. 415, pp. 24-30.
Jeremy P. Derrick et al., "Crystal structure of a streptococcal protein G domain bound to an Fab fragment", Nature, 1992, vol. 359, p. 752-754.
David Baker et al., "Protein Structure Prediction and Structural Genomics", Science, 2001, vol. 294, No. 5540, p. 93-96.
Teresa K. Attwood, "The Babel of Bioinformatics", Science, 2000, vol. 290, No. 5491, pp. 471-473.
Sauer-Eriksson et al., "Crystal structure of the C2 fragment of streptococcal protein G in complex with the Fc domain of human IgG", Structure, 1995, vol. 3, No. 3, pp. 265-278.

* cited by examiner

*Primary Examiner* — Daniel E Kolker
*Assistant Examiner* — James L Rogers
(74) *Attorney, Agent, or Firm* — Wenderoth, Lind & Ponack, L.L.P.

(57) ABSTRACT

An object of the present invention is to provide a Fab region-binding peptide having an excellent ability for binding to a Fab region of IgG, an affinity separation matrix having the peptide as a ligand, and a method for producing a Fab region-containing protein, the method using the affinity separation matrix. Further, another object of the present invention is to provide a DNA encoding for the peptide, a vector containing the DNA, and a transformant which has been transformed by the vector. The Fab region-binding peptide according to the present invention is characterized in having a mutation at a specific site in comparison with wild-type SpG-β1.

8 Claims, 3 Drawing Sheets

Specification includes a Sequence Listing.

FAB REGION-BINDING PEPTIDE

TECHNICAL FIELD

The present invention relates to a Fab region-binding peptide having an excellent ability for binding to a Fab region of IgG; an affinity separation matrix having the peptide as a ligand; a method for producing a Fab region-containing protein, the method using the affinity separation matrix; a DNA encoding for the peptide; a vector containing the DNA; and a transformant which has been transformed by the vector.

BACKGROUND ART

One of the important protein functions includes a function specifically binding to a specific molecule. This function plays an important role in immunoreaction and signal transduction in the body. Technologies using the function to separate and purify useful substances are actively developed. One example actually used for industrial purposes includes a protein A affinity separation matrix (hereinafter, protein A may be abbreviated as "SpA") which is used to purify (capture) an antibody medicine from an animal cell culture with a high purity at a time (Non-Patent Documents 1 and 2).

Antibody medicines which have been developed so far are generally monoclonal antibodies. These antibodies are mass-produced by using recombinant cell culture technology or the like. The "monoclonal antibodies" refer to antibodies produced by clones of a single antibody-producing cell. Almost all antibody medicines currently available on the market are classified into immunoglobulin G (IgG) subclasses based on their molecular structures. Further, clinical development of antibody medicines composed of antibody derivatives having molecular structures of fragmented immunoglobulins (fragment antibodies) has been actively conducted. A plurality of antibody medicines composed of immunoglobulin Fab fragments has been available on the market (Non-Patent Document 3).

In an initial purification step in antibody medicine production process, the above-described SpA affinity separation matrix is used. However, SpA is generally a protein that specifically binds to an Fc region of IgG. Accordingly, fragment antibodies that do not include the Fc region cannot be subjected to capturing using the SpA affinity separation matrix. Therefore, from the viewpoint of making the antibody medicine purification process into a platform, there are great industrial needs for the affinity separation matrix capable of capturing fragment antibodies that do not include the Fc region of IgG.

A plurality of proteins that bind to regions other than the Fc region of IgG has been already known (Non-Patent Document 4). However, there is no fact that the affinity separation matrix using such proteins as ligands is used for standard industrial purposes of purification of the antibody medicine, similarly to the SpA affinity separation matrix.

For example, a protein called protein G found in group G of Streptococcus sp. (hereinafter, protein G may be abbreviated as "SpG") has a property of binding to IgG. Also, there is an SpG affinity separation matrix product having SpG immobilized thereon as a ligand (product name: "Protein-G Sepharose 4 Fast Flow", manufactured by GE Healthcare, Patent Document 1). It is known that SpG strongly binds to the Fc region of IgG, but weakly binds to the Fab region (Non-Patent Documents 4 and 5). However, since the binding force of SpG to the Fab region is weak, it can be said that the SpG affinity separation matrix product has a low retention performance for fragment antibodies that do not include the Fc region, but include only the Fab region. Consequently, an attempt is being carried out to improve the binding force to the Fab region by introducing a mutation into the SpG (Patent Document 2).

PRIOR ART DOCUMENT

Patent Document

Patent Document 1: JP S63-503032 T
Patent Document 2: JP 2009-195184 A

Non-Patent Document

Non-Patent Document 1: Hober S. et al., J. Chromatogr, B, 2007, vol. 848, pages 40-47
Non-Patent Document 2: Shukla A. A. et al., Trends Biotechnol., 2010, vol. 28, pages 253-261
Non-Patent Document 3: Nelson A. N. et al., Nat. Biotechnol., 2009, vol. 27, pages 331-337
Non-Patent Document 4: Bouvet P. J., Int. J. Immunopharmac., 1994, vol. 16, pages 419-424
Non-Patent Document 5: Derrick J. P., Nature, 1992, vol. 359, pages 752-754

DISCLOSURE OF THE INVENTION

Problems to be Solved by the Invention

As described above, as an affinity ligand to adsorb antibodies and purify them, protein A (SpA) has been conventionally in practical use. The SpA has a specific affinity for only the Fc region of IgG. However, recently, there is a need for ligands having an affinity for the Fab region of IgG in terms of the fact that the technologies of using fragments of antibodies as medicines have been developed. Protein G (SpG) is known as a protein having an affinity for not only the Fc region but also the Fab region; however, its affinity for the Fab region is lower than that for the Fc region. As described in the invention of Patent Document 2, the attempt for improving the affinity to the Fab region by introducing a mutation into SpG is also examined. However, as for the mutant SpG described in Patent Document 2, the mutant SpG having an affinity to the Fab region, the affinity being not less than 5-fold higher than that to the Fc region, is not obtained. The affinity for the Fab region of the wild-type SpG is not high enough. Thus, the mutant SpG cannot be said to be sufficient as, for example, a ligand to purify antibody fragments including no Fc region.

Therefore, an object of the present invention is to provide a Fab region-binding peptide having an excellent ability for binding to a Fab region of IgG, an affinity separation matrix having the peptide as a ligand, and a method for producing a Fab region-containing protein, the method using the affinity separation matrix. Further, another object of the present invention is to provide a DNA encoding for the peptide, a vector containing the DNA, and a transformant which has been transformed by the vector.

Means for Solving the Problems

The present inventors have conducted intensive studies in order to solve the problems. As a result, they have obtained many protein G mutants by using a genetic engineering procedure, and then compared and examined the binding force to a Fab fragment antibody. Thus, they have succeeded in identifying the mutation position which improves the binding force and completed the present invention.

Hereinafter, the present invention is described.

[1] A Fab region-binding peptide represented by any one of the following (1) to (3):

(1) a Fab region-binding peptide having an amino acid sequence of SEQ ID NO: 1 derived from the β1 domain of protein G with substitution of an amino acid residue at not less than one position selected from the 13th, 19th, 30th and 33rd positions, and having a higher binding force to the Fab region of immunoglobulin than that before introduction of the substitution;

(2) a Fab region-binding peptide having an amino acid sequence specified in the (1) with deletion, substitution and/or addition of not more than 1 and not more than 20 amino acid residues at a region other than the 13th, 19th, 30th and 33rd positions, and having a higher binding force to the Fab region of immunoglobulin than the peptide having the amino acid sequence of SEQ ID NO: 1;

(3) a Fab region-binding peptide having an amino acid sequence having not less than 80% sequence identity to the amino acid sequence specified in the (1), and having a higher binding force to the Fab region of immunoglobulin than the peptide having the amino acid sequence of SEQ ID NO: 1, wherein the substituted amino acid residue at not less than 1 position selected from the 13th, 19th, 30th, and 33rd positions of the amino acid sequence specified in the (1) is not further mutated in the (3).

[2] The Fab region-binding peptide according to the [1], wherein the amino acid residue at the 13th position of the amino acid sequence specified in the (1) is substituted.

[3] The Fab region-binding peptide according to the [2], wherein the amino acid residue at the 13th position is substituted by Thr or Ser.

[4] The Fab region-binding peptide according to any one of the [1] to [3], wherein the amino acid residue at the 30th position of the amino acid sequence specified in the above (1) is substituted by Val, Leu or Ile.

[5] The Fab region-binding peptide according to any one of the [1] to [4], wherein the amino acid residue at the 19th position of the amino acid sequence specified in the (1) is substituted by Val, Leu or Ile.

[6] The Fab region-binding peptide according to any one of the [1] to [5], wherein the amino acid residue at the 33rd position of the amino acid sequence specified in the (1) is substituted by Phe.

The Fab region-binding peptide according to any one of the [1] to [6], wherein the position of deletion, substitution and/or addition of an amino acid residue is at least one position selected from the 2nd, 10th, 15th, 18th, 21st, 22nd, 23rd, 24th, 25th, 27th, 28th, 31st, 32nd, 35th, 36th, 39th, 40th, 42nd, 45th, 47th and 48th positions of the amino acid sequence specified in the (2).

[8] The Fab region-binding peptide according to any one of the [1] to [6], wherein the position of deletion, substitution and/or addition of an amino acid residue is an N-terminus and/or a C-terminus of the amino acid sequence specified in the (2).

[9] The Fab region-binding peptide according to any one of the [1] to [8], wherein the sequence identity to the amino acid sequence specified in the (3) is not less than 95%.

[10] A Fab region-binding peptide multimer, having not less than 2 domains wherein not less than 2 Fab region-binding peptides according to any one of the [1] to [9] are connected with one another.

[11] An affinity separation matrix, wherein a Fab region-binding peptide according to any one of the [1] to [9] or a Fab region-binding peptide multimer according to the [10] is immobilized on a water-insoluble carrier as a ligand.

[12] A method for producing a Fab region-containing protein, comprising the steps of contacting the affinity separation matrix according to the [11] with a liquid sample containing the Fab region-containing protein, and separating the Fab region-containing protein bound to the affinity separation matrix from the affinity separation matrix.

[13] A DNA, encoding the Fab region-binding peptide according to any one of the [1] to [9].

[14] A vector, containing the DNA according to the [13].

[15] A transformant, transformed by the vector according to the [14].

Effect of the Invention

Since the Fab region-binding peptide according to the present invention has a sufficiently high affinity for the Fab region of IgG, it has an affinity for not only normal antibodies but also antibody fragments that have the Fab region, but do not have the Fc region. Accordingly, an affinity separation matrix having the Fab region-binding peptide of the present invention immobilized on an insoluble carrier allows for efficient purification of antibody fragment medicines. Thus, in recent years, antibody fragment medicines have been actively developed for the reason of achieving low cost production, etc. The present invention contributing to the practical use of antibody fragment medicines is very important from the industrial viewpoint.

More specifically, in the present invention, a plurality of mutant SpGs having an affinity to the Fab region, the affinity being surprisingly about 10-fold higher than that to the Fc region, is obtained. Further, mutant SpGs having an affinity to the Fab region, the affinity being more surprisingly not less than 50-fold higher than that to the Fc region, are obtained. Thus, the present invention not only has succeeded in obtaining an affinity durable for practical use as the ligand to purify antibody fragments including no Fc region but also has provided various mutation procedures for achieving various levels of affinity. The dissociation rate constant of the mutant SpG obtained in the present invention is significantly smaller than that of the wild-type SpG. A plurality of mutant SpGs obtained has a dissociation rate constant of not more than ½. Surprisingly, some mutants obtained have a dissociation rate constant of 1/10. When the dissociation rate constant of the ligand is increased, improvement in the retention performance of the affinity separation matrix having the ligand immobilized thereon for proteins containing the Fab region is expected. On these points, it can be said that the present invention exhibits effects superior to the invention described in Patent Document 2.

MODE FOR CARRYING OUT THE INVENTION

Figure 1:
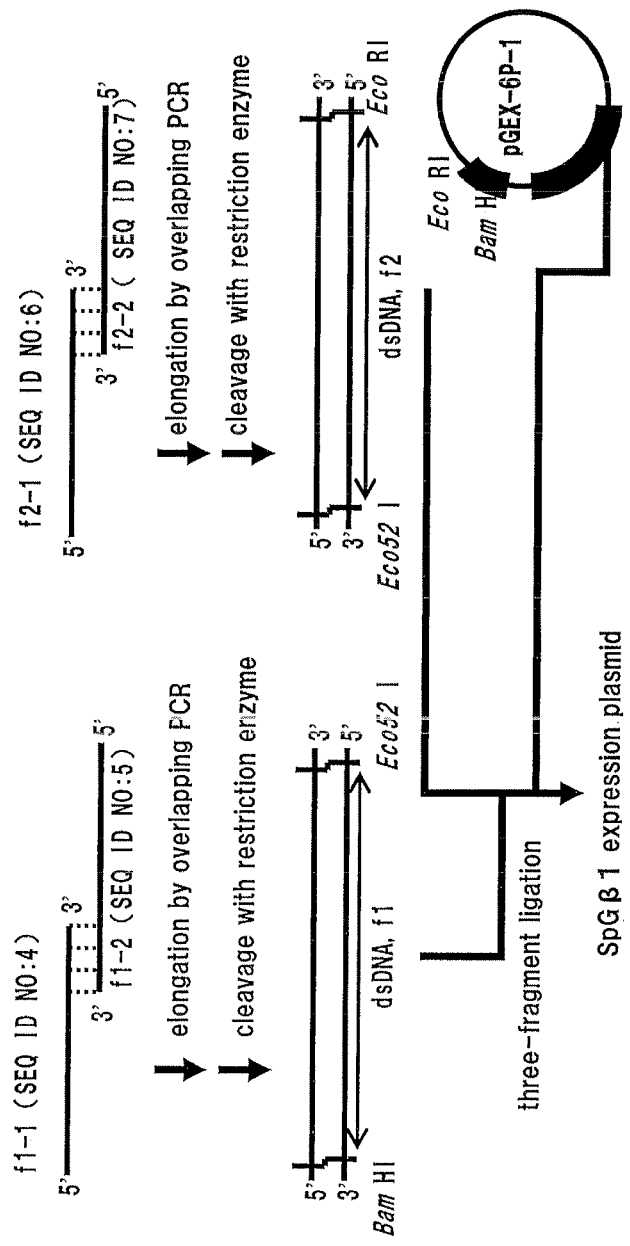
FIG. 1 is a view showing a method for producing a wild-type SpG-β1 expression plasmid.

The Fab region-binding peptide (1) according to the present invention is a Fab region-binding peptide having an amino acid sequence of SEQ ID NO: 1 derived from the β1 domain of protein G (SpG) with substitution of an amino acid residue at not less than one position selected from the 13th, 19th, 30th and 33rd positions, and having a higher binding force to the Fab region of immunoglobulin than that before introduction of the substitution The term "immunoglobulin" means a glycoprotein produced by B cells of lymphocytes and has a function to recognize molecules such as specific proteins and to bind to them. The immunoglobulin has a function to specifically bind to the specific molecules (antigens) and a function to detoxify and remove antigen-containing factors in cooperation with other biological molecules or cells. The immunoglobulin is generally referred to as "antibody", and the name is inspired by such functions. Basically, all immunoglobulins have the same molecular structure. The basic structure of immunoglobulins is a Y-shaped four-chain structure (two polypeptide chains with two light and heavy chains). There are two types of light chains (L chains): λ and κ chains. All the immunoglobulins have either of these types. There are five types of heavy chains (H chains): γ, μ, α, δ, and ε chains, all having different structures. The type (isotype) of immunoglobulin varies depending on the differences in the heavy chains. Immunoglobulin G (hereinafter, may be abbreviated as "IgG") is a monomer immunoglobulin, is composed of two heavy chains (γ chains) and two light chains, and has two antigen binding sites.

The vertical lower half part of the "Y" in immunoglobulin is called "Fc region". The upper half part of the "V" is called "Fab region". The Fc region has an effector function to initiate a reaction after binding of an antibody to an antigen, while the Fab region has a function to bind to an antigen. The Fab and Fc regions of heavy chains are connected by the hinge region. The proteolytic enzyme papain contained in papaya degrades the hinge region to cut into two Fab regions (fragments) and one Fc region. The portion (domain) close to the end of the "Y" of the Fab regions is called "variable region (V region)" because there are various changes in amino acid sequences in order to bind to various antigens. The light chain variable region is called "VL region", while the heavy chain variable region is called "VH region". The Fab and the Fc regions other than the V region are regions with relatively less change and are called "constant region (C region)". The light chain constant region is called "CL region", while the heavy chain constant region is called "CH region". The CH region is further divided into three regions: CH1 to CH3. The heavy chain Fab region is composed of the VH region and the CH1. The heavy chain Fc region is composed of the CH2 and CH3 regions. The hinge region is located between the CH1 and CH2 regions. More specifically, the binding of SpG-β to IgG indicates the binding of IgG to the CH1 region (CH1γ) and the CL region. Particularly, the binding to the CH1 region is main binding (Non-Patent Document 5).

The Fab region-binding peptide according to the present invention binds to the Fab region of IgG. The Fab region-containing protein to which the peptide of the present invention binds may be a protein including the Fab region, or may be an IgG molecule containing enough Fab and Fc regions, or may be a molecule derivative of IgG. The molecule derivative of IgG to which the Fab region-binding peptide of the present invention binds is not particularly limited as long as it is a derivative having the Fab region. Examples thereof may include a Fab fragment in which only the Fab region of IgG is cleaved; chimeric igg in which x a part of the human IgG domain is replaced and fused with the IgG domain of other species; IgG in which the sugar chain in the Fc region is subjected to molecular modification; and a Fab fragment obtained by covalent bonding of an agent or the like.

The term "peptide" as used herein is a peptide including all molecules having a polypeptide structure. It includes not only so-called proteins, but also fragmented proteins and proteins to which other peptides are bound by the peptide bond or the like.

The term "protein G (SpG)" is a protein derived from a cell wall of the group G of *Streptococcus* sp. The SpG has an ability to bind to IgG of almost all mammals. The SpG strongly binds to the Fc region of IgG and weakly binds to the Fab region of IgG.

The functional domain showing the IgG-binding property of SpG is called "β domain (SpG-β)". The domain may be called either "β (B) domain" or "C domain" (refer to Akerstrom et al., J. Biol. Chem., 1987, 28, 13388-, FIG. 5). In the present specification, it is called "β domain" in accordance with the definition of Fahnestock et al. (Fahnestock et al., J. Bacteriol., 1986, 167, 870-).

The details of the amino acid sequence of SpG-β, vary depending on bacterial species and strains to be derived from. As for typical amino acid sequences of two β domains (β1 and β2) derived from strain GX7809 of the group G of *Streptococcus* sp., the amino acid sequence in which Asp at the 1st position of the β1 domain (SpG-β1) is substituted by Thr is shown in SEQ ID NO: 1, and the amino acid sequence of the β2 domain (SpG-β2) is shown in SEQ ID NO: 2. The amino acid sequences of the respective β domains of SpG have high sequence homology with each other. These sequences are collectively called "protein G-β domain (SpG-β). In this regard, the 1st position of SpG-β2 derived from strain GX7809 is Thr. Further, depending on references, the sequences after the 2nd position of SEQ ID NOs: 1 and 2 correspond to amino acid sequences of respective domains of SpG. The above substitution has no influence on the affinity of the peptide having the amino acid sequence of SEQ ID NO: 1 to the Fab region.

As indicated by Alexander et al. (Alexander et al., Biochemistry, 1992, 31, 3597-), the denaturation midpoint temperatures of SpG-β1 and SpG-β2 at pH 5.4 are 87.5° C. and 79.4° C., respectively. Therefore, one of the preferred embodiments of the present invention is to use SpG-β1 (SEQ ID NO: 1) as a mutagenesis target from the viewpoint of thermal stability of peptides. However, in the case where an amino acid sequence finally obtained by adding a mutation to the amino acid sequence is included in the scope of the present invention, the mutagenesis target is not limited to SpG-β1 (SEQ ID NO: 1). For example, the mutagenesis target may be SpG-β2 (SEQ ID NO: 2), the domain (SpG-C2) situated in the second from the N-terminal side of three IgG-binding domains contained in SpG derived from strain G148 or strain GX7805 of the group G of *Streptococcus* sp., or a publicly-known SpG mutant having excellent thermal stability (refer to WO1997-026930 and JP 2003-88381 A).

The term "domain" refers to a higher-order protein structural unit composed of several tens or hundreds of amino acid residues, which is capable of fully exhibiting a certain physicochemical or biochemical function.

The "mutant" of a protein or a peptide refers to a protein or a peptide in which a wild-type protein or peptide sequence has at least one of substitution, addition and deletion at the amino acid level.

The present invention relates to a peptide having a sequence in which a mutation is introduced into the wild-type SpG-β. The amino acid sequence before introduction of the mutation is an amino acid sequence of SpG-β1 shown as SEQ ID NO: 1. However, even a peptide obtained by adding a mutation to the amino acid sequence of SEQ ID NO: 2 is included in the scope of the present invention as long as it is included in any of the Fab region-binding peptides (1) to (3) according to the present invention.

Regarding the description of a mutation to substitute an amino acid, a wild-type or non-mutant amino acid residue is described in front of the number of a substitution position, and a mutant amino acid residue is described after the number of a substitution position. For example, a mutation to substitute the Gly residue at the 29th position with Ala is indicated by G29A.

The present invention is a technology for introducing an amino acid substitution mutation into the β1 domain of the wild-type SpG to produce a mutation having a binding force to the Fab region of immunoglobulin G higher than that before introduction of the amino acid mutation. The substitution position of the amino acid residue of the present invention is any of the 13th (Lys), 19th (Glu), 30th (Phe), and 33rd (Tyr) positions in the amino acid sequence of SEQ ID NO: 1. Even if the number of amino acids in the amino acid sequence before introduction of the mutation is different, when the sequence identity is not less than 80%, those skilled in the art are able to easily identify the position corresponding to the 13th, 19th, 30th or 33rd position in SEQ ID NO: 1. Specifically, these positions can be confirmed by aligning the sequences using a multiple alignment program for amino acid sequences: Clustal (http://www.clustal.org/omega/).

The Fab region-binding peptide (1) according to the present invention has an amino acid sequence of SEQ ID NO: 1 derived from the β1 domain of protein G with substitution of an amino acid residue at not less than one position selected from the 13th, 19th, 30th and 33rd positions. The types of amino acids to mutate are not particularly limited, and examples thereof include a substitution by non-protein-constituting amino acids and non-natural amino acids. In terms of genetic engineering production, natural amino acids can be suitably used. Further, the natural amino acids are classified into the categories of neutral amino acids; acidic amino acids such as Asp and Glu; and basic amino acids such as Lys, Arg, and His. The neutral amino acids are classified into the categories of aliphatic amino acids; imino acids such as Pro; and aromatic amino acids such as Phe, Tyr, and Trp. Further, the aliphatic amino acids are classified into the categories of Gly; Ala; branched amino acids such as Val, Leu, and Ile; hydroxy amino acids such as Ser and Thr; sulfur-containing amino acids such as Cys and Met; and acid amide amino acids such as Asn and Gln. Further, since Tyr has a phenolic hydroxyl group, it may be classified into not only aromatic amino acids but also hydroxy amino acids. Further, from another viewpoint, the natural amino acids may also be classified into the categories of nonpolar amino acids with high hydrophobicity such as Gly, Ala, Val, Leu, Ile, Trp, Cys, Met, Pro, and Phe; neutral polar amino acids such as Asn, Gln, Ser, Thr, and Tyr; acidic polar amino acids such as Asp and Glu; and basic polar amino acids such as Lys, Arg, and His. In the case where an improvement in the binding force to the Fab region is observed in peptides in which the amino acid residues at the above positions are substituted, it is highly possible that an improvement in the binding force to the Fab region is similarly observed even in peptides in which the substituted amino acids are mutated to the amino acids as being in the same categories as above.

The substitution mutation in the present invention preferably includes a mutation in which the amino acid residue at the 13th position is substituted by Thr or Ser, a mutation in which the amino acid residue at the 30th position is substituted by Val, Leu or Ile, and/or a mutation in which the amino acid residue at the 19th position is substituted by Val, Leu or Ile. Further, it is more preferable to include a mutation in which the amino acid residue at the 13th position is substituted by Thr or Ser and include a mutation in which the amino acid residue at the 30th position is substituted by Val, Leu or Ile and/or a mutation in which the amino acid residue at the 19th position is substituted by Val, Leu or Ile. Furthermore, it is more preferable to include a mutation in which the amino acid residue at the 13th position is substituted by Thr or Ser and include a mutation in which the amino acid residue at the 30th position is substituted by Val, Leu or Ile and/or a mutation in which the amino acid residue at the 19th position is substituted by Ile or Val and include a mutation in which the amino acid residue at the 33rd position is substituted by Phe. More preferably, the amino acid residue at the 30th position is substituted by Leu, and the amino acid residue at the 19th position is substituted by Val or Ile.

The Fab region-binding peptide (1) according to the present invention has characteristics such that the binding force to the Fab region of IgG is higher than that before introduction of the amino acid substitution. The Affinity for the Fab region of IgG can be measured by, for example, a biosensor such as a Biacore system using surface plasmon resonance principle (manufactured by GE Healthcare). However, the measuring method is not limited thereto.

The measurement condition of the binding property to the Fab region may be determined so that a binding signal when binding to the Fab region of IgG can be detected. The binding property can be easily evaluated at a temperature of 20 to 40° C. (constant temperature) and a neutral pH of 6 to 8.

The IgG molecule as a binding partner is not particularly limited as long as it allows detection of binding to the Fab region. The binding to the Fc region is also detected in the case of using an IgG molecule containing the Fc region. Thus, it is preferable to use Fab fragments obtained by cleaving the Fab region so as to remove the Fc region and separating and purifying the resultant fragments. The difference in affinity can be easily analyzed by those skilled in the art by obtaining sensorgrams of the binding reactions with the same IgG molecule in the same measurement condition, and comparing a peptide before introduction of the mutation with a peptide after introduction of the mutation using a binding parameter obtained by analysis.

Examples of binding parameters that can be used include the affinity constant ($K_A$) and the dissociation constant ($K_D$) (Nagata et al., "Real-time analysis experiment of biomaterial interactions", Springer-Verlag Tokyo, 1998, page 41). The affinity constant ($k_A=k_{on}/k_{off}$) is a value obtained by dividing the binding rate constant ($k_{on}$) by the dissociation rate constant ($k_{off}$). Accordingly, when the binding rate constant is a larger value or when the dissociation rate constant is a smaller value, the affinity constant increases. Particularly, the dissociation rate constant is an indicator for the separation tendency of two interacting molecules. Accordingly, it can be said when the dissociation rate constant is small, the retention performance of the affinity separation matrix having the peptide of the present invention immobilized thereon for the Fab fragment is high. Therefore, a peptide having a dissociation rate constant ($k_{off}$) of not more than ½ of the dissociation rate constant of the peptide having a sequence before introduction of the mutation can be suitably used as the peptide of the present invention with a mutation-introduced sequence. Further, the peptide that can be suitably used is a peptide having a dissociation rate constant of more preferably not more than ⅓, further more preferably not more than ¼, further more preferably not more than ⅕, and particularly preferably not more than ¹⁄₁₀ of the above dissociation rate constant.

The affinity constant between the mutation according to the present invention and the Fab fragment can be determined, for example, by using an experimental system in which a Biacore system is used, a Fab fragment is immobilized on a sensor chip, and the mutation of the present invention is added to a flow channel under the condition of a temperature of 25° C. and a pH of 7.4. As for the peptide of the present invention having a sequence in which a mutation is introduced, a peptide having an affinity constant ($k_A$) which is not less than 2-fold higher than the affinity constant of the peptide having a sequence before introduction of the mutation can be used. Further, the peptide that can be suitably used is a peptide having an affinity constant of more preferably not less than 3-fold, further more preferably not less than 5-fold, further more preferably not less than 6-fold, further more preferably not less than 7-fold, further more preferably not less than 10-fold, further more preferably not less than 20-fold, and particularly preferably not less than 50-fold higher than the above affinity constant.

The Fab region-binding peptide (2) according to the present invention is a Fab region-binding peptide having an amino acid sequence specified in the (1) with deletion, substitution and/or addition of one or several amino acid residues at a region other than the 13th, 19th, 30th and 33rd positions, and having a higher binding force to the Fab region of immunoglobulin than the peptide having the amino acid sequence of SEQ ID NO: 1.

The range of "one or several" in "deletion, substitution and/or addition of one or several amino acid residues" is not particularly limited as long as the Fab region-binding peptide having deletion or the like has a high binding force to the Fab region of IgG. The range of "one or several" may be, for example, not less than 1 and not more than 20, preferably not less than 1 and not more than 15, more preferably not less than 1 and not more than 10, further more preferably not less than 1 and not more than 7, still further preferably not less than 1 and not more than 5, and particularly preferably not less than 1 and not more than 3, not less than 1 and not more than 2, or about 1.

In the amino acid sequence of the Fab region-binding peptide (2) according to the present invention, the position of deletion, substitution, and/or addition of an amino acid residue is not particularly limited as long as it is any position other than the 13th, 19th, 30th, and 33rd positions specified in the Fab region-binding peptide (1). For example, at least one position selected from the 2nd, 10th, 15th, 18th, 21st, 22nd, 23rd, 24th, 25th, 27th, 28th, 31st, 32nd, 35th, 36th, 39th, 40th, 42nd, 45th, 47th, and 48th positions is preferred. These positions are particularly preferred as the positions to be substituted.

The types of amino acids with which the amino acid residues at the above positions are substituted are not particularly limited. For example, the 2nd position is preferably Arg, the 10th position is preferably Arg, the 15th position is preferably a neutral polar amino acid such as Gln or Thr, the 18th position is preferably Ala, the 21st position is preferably Ile, Ala or Asp, the 22nd position is preferably Asn or Glu, the 23rd position is preferably Thr or Asp, the 24th position is preferably Thr, the 25th position is preferably Ser or Met, the 27th position is preferably Asp or Gly, the 28th position is preferably Arg, Asn or Ile, the 31st position is preferably Arg, the 32nd position is preferably Arg, the 35th position is preferably an aromatic amino acid such as Phe or Tyr, the 36th position is preferably Gly, the 39th position is preferably Leu or Ile, the 40th position is preferably Val or Glu, the 42nd position is preferably Leo, Val or Gin, the 45th position is preferably Phe, the 47th position is preferably His, Asn, Ala, Gly or Tyr, and the 48th position is preferably an amino acid which is substituted by Thr. Particularly, the 2nd position is preferably Arg, the 10th position is preferably Arg, the 15th position is preferably kinds of neutral polar amino acids, the 18th position is preferably Ala, the 21st position is preferably Ala or Asp, the 39th position is preferably Leu or Ile, and the 47th position is preferably Ala.

Other than the above examples, the positions to be substituted includes at least one selected from the 6th, 7th, 24th, 28th, 29th, 31st, 35th, 40th, 42nd, and 47th positions in which the types of amino acids are different between the wild-type SpG-β and the publicly-known SpG-β mutation.

In the amino acid sequence of the Fab region-binding peptide (2) according to the present invention, the position of deletion, substitution, and/or addition of an amino acid residue includes an N-terminus and/or a C-terminus. These positions are particularly preferred as the positions of deletion and/or addition.

The binding force of the Fab region-binding peptide (2) according to the present invention to the Fab region of IgG can be measured in the same manner as in the above Fab region-binding peptide (1).

The Fab region-binding peptide (3) according to the present invention is a Fab region-binding peptide having an amino acid sequence having not less than 80% sequence identity to the amino acid sequence specified in the (1), and having a higher binding force to the Fab region of immunoglobulin than the peptide having the amino acid sequence of SEQ ID NO: 1, wherein the substituted amino acid residue at not less than 1 position selected from the 13th, 19th, 30th, and 33rd positions of the amino acid sequence specified in the (1) is not further mutated in the (3).

The above-described sequence identity is preferably not less than 85%, more preferably not less than 90%, not less than 95%, not less than 98%, or not less than 99%, and particularly preferably not less than 99.5%.

As described in the Fab region-binding peptide (1), the above sequence identity can be measured by using the multiple alignment program for amino acid sequences: Clustal (http://www.clustal.org/omega/). Further, the binding force of the Fab region-binding peptide (3) according to the present invention to the Fab region of IgG can also be measured in the same manner as in the Fab region-binding peptide (1).

SpG is a protein containing two or three immunoglobulin-binding domains arranged in tandem. As one embodiment, the Fab region-binding peptide of the present invention may be also a multimer of a plurality of domains in which not less than 2, preferably not less than 3, more preferably not less than 4, and more preferably not less than 5 Fab region-binding peptides serving as monomers or single domains are connected with one another. The upper limit of the number of domains to be connected is not more than 10, preferably not more than 8, and more preferably not more than 6. The multimer may be a homopolymer, such as homodimer or homotrimer, in which single Fab region-binding peptides are connected together, or a heteropolymer, such as a heterodimer or heterotrimer, in which a plurality of types of Fab region-binding peptides is connected with one another.

Examples of the connection between monomer peptides to be obtained by the present invention include, but are not limited to, a connection by one or more amino acid residues and a direct connection without the insertion of amino acid residues. The number of amino acid residues involved in the connection is not particularly limited, but is preferably not more than 20 residues, more preferably not more than 15 residues, further more preferably not more than 10 residues, further more preferably not more than 5 residues, and furthermore preferably not more than 2 residues. It is preferable to use a sequence connecting between the wild-type SpG-β1 and the wild-type SpG-β2. Preferably, the connection does not destabilize the three-dimensional conformation of the monomer peptides from another viewpoint.

One embodiment includes a fusion peptide, wherein one component such as the Fab region-binding peptide to be obtained by the present invention or a peptide multimer having two or more Fab region-binding peptides connected thereto is fused to another peptide having a different function. Examples of the fusion peptide may include, but are not limited to, fusion peptides with albumin and GST (glutathione S-transferase). Fusion peptides with a nucleic acid such as a DNA aptamer, a drug such as antibiotic substance, or a polymer such as PEG (polyethylene glycol) are also included in the scope of the present invention as long as these fusion peptides make use of the advantages of the peptide obtained by the present invention.

One embodiment of the present invention also includes the use of the peptide of the present invention as an affinity ligand characterized by having an affinity for IgG or its fragment, particularly for the Fab region. Similarly, one embodiment also includes an affinity separation matrix, characterized in that the ligand is immobilized on a water-insoluble carrier. The term "affinity ligand" refers to a substance or functional group that selectively captures (binds to) a target molecule from a group of molecules based on specific affinity between molecules such as an antigen and antibody binding, and refers herein to a peptide that specifically binds to IgG. The term "ligand" as used alone herein is synonymous with an "affinity ligand".

Examples of the water-insoluble carrier used in the present invention include inorganic carriers such as glass beads and silica gel; organic carriers such as synthetic polymers including cross-linked polyvinyl alcohol, cross-linked polyacrylate, cross-linked polyacrylamide, and cross-linked polystyrene, and polysaccharides including crystalline cellulose, cross-linked cellulose, cross-linked agarose, and cross-linked dextran; and composite carriers of combinations of these carriers such as organic-organic and organic-inorganic composite carriers. Examples of commercial products thereof include GCL2000 serving as porous cellulose gel, Sephacryl S-1000 that is a covalently cross-linked copolymer of allyl dextran and methylene bisacrylamide, Toyopearl serving as acrylate carrier, Sepharose CL4B serving as cross-linked agarose carrier, and Cellufine serving as cross-linked cellulose carrier. However, it should be noted that the water-insoluble carrier usable in the present invention is not limited to the carriers listed above.

In view of the purpose and method for using the affinity separation matrix, the water-insoluble carrier used in the present invention desirably has a larger surface area and is preferably a porous matrix having a large number of fine pores with a suitable size. The carrier can be in any of bead, monolith, fiber, film (including hollow fiber) or the like, and any form can be selected.

Immobilization of the ligand on the carrier may be accomplished, for, example, by a conventional coupling method utilizing an amino, carboxyl or thiol group of the ligand. Examples of such a coupling method include an immobilization method including activation of a carrier by the reaction with cyanogen bromide, epichlorohydrin, diglycidyl ether, tosyl chloride, tresyl chloride, hydrazine, sodium periodate, etc., or introduction of a reactive functional group into the carrier surface, and the coupling reaction between the resulting carrier and a compound to be immobilized as a ligand; and an immobilization method involving condensation and crosslinking which includes adding a condensation reagent such as carbodiimide or a reagent having a plurality of functional groups in the molecule, such as glutaraldehyde, into a system containing a carrier and a compound to be immobilized as a ligand.

A spacer molecule composed of a plurality of atoms may be introduced between the ligand and the carrier, or alternatively, the ligand may be directly immobilized on the carrier. Accordingly, for immobilization, the Fab region-binding peptide according to the present invention may be chemically modified, or may include an additional amino acid residue useful for immobilization. Examples of the amino acids useful for immobilization include amino acids having a functional group useful for a chemical reaction for immobilization in a side chain, and specifically include Lys which includes an amino group in a side chain and Cys which includes a thiol group in a side chain. The essence of the present invention is to similarly provide the Fab region-binding property imparted to the peptide of the present invention to the matrix including as a ligand the peptide immobilized therein. This is included within the scope of the present invention even if the peptide of the present invention is modified or altered in any manner for immobilization.

The affinity separation matrix of the present invention is used so that the peptides containing the Fab region of IgG can be separated and purified by affinity column chromatography purification. These peptides containing the Fab region of IgG can be purified by procedure in accordance with IgG affinity column chromatography purification using, for example, the SpA affinity separation matrix (Non-Patent Document 1). Specifically, a buffer containing a peptide containing the Fab region of IgG is prepared (the pH: around neutral), and the solution is allowed to pass through an affinity column filled with the affinity separation matrix of the present invention, so that the peptide containing the Fab region of IgG is adsorbed. Next, the inside of the affinity column is washed by allowing an adequate amount of a pure buffer to pass through the column. At this point, the target peptide containing the Fab region of IgG is still adsorbed on the affinity separation matrix of the present invention in the column. The affinity separation matrix including the peptide obtained by the present invention as a ligand immobilized therein is excellent in the absorption and retention performances of a target peptide containing the Fab region of IgG in the steps from the step for adding this sample to the step for washing the matrix. Then, an acid buffer (optionally containing a substance for promoting dissociation from the matrix) with a pH appropriately adjusted is allowed to pass through the column, so that the target peptide containing the Fab region of IgG is eluted. Accordingly, this purification procedure achieves high purity.

Reuse of the affinity separation matrix of the present invention is enabled by allowing an adequate strong acid or strong alkali pure buffer which does not completely impair the functions of the ligand compound or the base material of the carrier (or optionally a solution containing an adequate modifying agent or an organic solvent) to pass through the column, followed by washing of the matrix.

The present invention also relates to a DNA encoding the peptide according to the present invention. The DNA encoding the peptide of the present invention may be any DNA as long as the amino acid sequence produced from translation of the base sequence of the DNA constitutes the peptide. Such a base sequence can be obtained by common known techniques, for example, using polymerase chain reaction (hereinafter, abbreviated as "PCR") technology. Alternatively, such a base sequence can be synthesized by publicly-known chemical synthesis techniques or is available from DNA libraries. A codon in the base sequence may be substituted by a degenerate codon, and the base sequence is not necessarily the same as the original base sequence as long as the translated amino acids are the same as those encoded by the original base sequence. It is possible to obtain a recombinant DNA having the one or more base sequences, a vector containing the recombinant DNA, such as a plasmid or a phage, a transgenic microorganism or cell transformed by the vector having the DNA, a genetically engineered organisms having the DNA introduced therein, or a cell-free protein synthesis system using the DNA as a template for transcription.

The Fab region-binding peptide according to the present invention may be available in the form of a fusion peptide with a protein that is publicly-known to beneficially facilitate assistant action for expression of a protein or purification of a protein. That is, it is possible to obtain a microorganism or cell containing at least one recombinant DNA encoding a fusion peptide containing the Fab region-binding peptide according to the present invention. Examples of such fusion, proteins include, but are not limited to, a maltose-binding protein (MBP) and a glutathione S-transferase (GST).

Site-directed mutagenesis for modifying the DNA encoding the peptide of the present invention can be carried out as follows, using recombinant DNA technology, PCR technology or the like.

That is, mutagenesis by recombinant DNA technology can be carried out as follows: for example, in the case where there are suitable restriction enzyme recognition sequences on both sides of a mutagenesis target site in the gene encoding the peptide of the present invention, cassette mutagenesis can be used in which a region containing the mutagenesis target site is removed by cleaving these restriction enzyme recognition site with restriction enzymes and a mutated DNA fragment is inserted only into the target site by a method such as chemical synthesis.

Further, in the case of site-directed mutagenesis by PCR, for example, double primer mutagenesis can be used in which PCR is carried out by using a double-stranded plasmid encoding the peptide of the present invention as a template, and two kinds of synthesized oligo primers which contain complementary mutations in the + and − strands.

Further, a DNA encoding a multimer peptide can be produced by ligating the desired number of DNAs each encoding the monomer peptide (single domain) of the present invention to one another in tandem. For example, ligation to produce the DNA encoding a multimer peptide can be accomplished by introducing a suitable restriction enzyme site into the DNA sequences, and ligating double-stranded DNA fragments cleaved with restriction enzyme using a DNA ligase. One restriction enzyme site may be introduced or a plurality of restriction enzyme sites of different types may be introduced. Further, in the case where the base sequences encoding monomer peptides in the DNA encoding a respective multimer peptide are the same, homologous recombination may be induced in a host. Thus, the ligated DNAs encoding monomer peptides have not more than 90% base sequence identity, preferably not more than 85% base sequence identity, more preferably not more than 80% base sequence identity, and further more preferably not more than 75% base sequence identity to one another. Further, the base sequence identity can be determined by an ordinary method, in the same manner as in the amino acid sequence.

The "expression vector" of the present invention includes a base sequence encoding the peptide of the above-described present invention or a part of the amino acid sequence of the peptide, and a promoter that can be operably linked to the base sequence to function in a host. Usually, the vector can be constructed by linking or inserting a gene encoding the peptide of the present invention to a suitable vector. The vector for insertion of the gene is not particularly limited as long as it is capable of autonomous replication in a host. As such a vector, a plasmid DNA or a phage DNA can be used. For example, in the case of using *Escherichia coli* as a host, a pQE series vector (manufactured by QIAGEN), a pET series vector (manufactured by Merck), a pGEX series vector (manufactured by GE Healthcare Bioscience) or the like can be used.

The transformant of the present invention can be produced by introducing the recombinant vector of the present invention into a host cell. Examples of the method for introducing the recombinant DNA into the host include, but are not limited to, method using calcium ions, electroporation method, spheroplast method, lithium acetate method, *agrobacterium* infection method, particle gun method and polyethylene-glycol method. Further, an example of the method for expressing the obtained gene function in the host includes method in which the gene obtained by the present invention is incorporated into the genome (chromosome). The host cell is not particularly limited. Preferred examples of those suited for low-cost mass production include *Escherichia coli*, *Bacillus subtilis*, and bacteria such as genera including *Brevibacillus*, *Staphylococcus*, *Streptococcus*, *Streptomyces*, and *Corynebacterium* (eubacteria).

The Fab region-binding peptide according to the present invention can be produced by culturing the above-described transformant in a medium; allowing the transformant to express and accumulate the peptide of the present invention in the cultured bacterial cell (including the periplasmic space of the bacterial cell) or in the culture solution (outside the bacterial cell); and collecting the desired peptide from the culture. Further, the peptide of the present invention can also be produced by culturing the above-described transformant in a medium; allowing the transformant to express and accumulate the fusion protein containing the peptide of the present invention in the cultured bacterial cell (including the periplasmic space of the bacterial cell) or in the culture solution (outside the bacterial cell); collecting the fusion peptide from the culture; cleaving the fusion peptide with a suitable protease; and collecting the desired peptide.

The transformant of the present invention can be cultured in a medium in accordance with a common method for culturing host cells. The medium used for culturing the produced transformant is not particularly limited as long as it enables high yield production of the peptide of the present invention at high efficiency. Specifically, carbon and nitrogen sources such as glucose, sucrose, glycerol, polypeptone, meat extracts, yeast extracts, and casamino acids can be used. In addition, the medium is supplemented, as required, with inorganic salts such as potassium salts, sodium salts, phosphates, magnesium salts, manganese salts, zinc salts, and iron salts. In the case of an auxotrophic host cell, nutritional substances necessary for its growth may be added to the medium. Moreover, antibiotics such as penicillin, erythromycin, chloramphenicol, and neomycin may be added as required.

Furthermore, a variety of publicly-known protease inhibitors, or phenylmethane sulfonyl fluoride (PMSF), benzamidine, 4-(2-aminoethyl)-benzenesulfonyl fluoride (AEBSF), antipain, chymostatin, leupeptin, pepstatin A, phosphoramidon, aprotinin, and ethylenediaminetetra acetic acid (EDTA), and/or other commercially available protease inhibitors may be added at appropriate concentrations in order to inhibit the degradation of the target peptide caused by a host-derived protease present inside or outside the bacterial cells.

In order to make accurate folding of the Fab region-binding-peptide according to the present invention, a molecular chaperone such as GroEL/ES, Hsp70/DnaK, Hsp90 and Hsp104/ClpB may be used (for example, such a molecular chaperone is co-expressed with the peptide of the present invention or is allowed to co-exist with the peptide of the present invention by combination into a fusion protein or the like). Further, other examples of techniques for accurate folding of the peptide of the present invention include, but are not limited to, such as addition of an additive for assisting accurate folding into the medium; and culturing at a low temperature.

Examples of the medium for culturing transformed cells produced from an *Escherichia coli* host include LB medium (triptone 1%, yeast extract 0.5%, NaCl 1%) or 2×YT medium (triptone 0.6%, yeast extract 1.0%, NaCl 0.5%) or the like.

Further, aerobic culture is carried out at a temperature of 15 to 42° C., preferably 20 to 37° C., for several hours to several days in an aeration-stirring condition. Thus, the peptide of the present invention is accumulated in the cultured cells (including the periplasmic space) or accumulated in the culture solution (extracellularly), and recovered therefrom. In some cases, the culture may be performed anaerobically without aeration. In the case where a recombinant peptide is secreted, the produced recombinant peptide can be recovered after the culture period by separating the cultured cells and the supernatant containing the secreted peptide through common separation methods such as centrifugation and filtration. Further, in the case where the peptide is accumulated in the cultured cells (including the periplasmic space), the peptide accumulated in the cells can be recovered, for example, by collecting the bacterial cells from the culture solution by centrifugation, filtration or the like, and then disrupting the bacterial cells by sonication, French press method or the like, and/or solubilizing the peptide by adding a surfactant or the like.

Purification of the peptide of the present invention can be accomplished by any one or an appropriate combination of techniques such as affinity chromatography, cation or anion exchange chromatography, gel filtration chromatography or the like. Examples of techniques to confirm whether the obtained purified product is a target peptide include common techniques such as SDS polyacrylamide gel electrophoresis, N-terminal amino acid sequence analysis, Western blot analysis or the like.

The present application claims a priority of Japanese Patent Application No. 2013-180249 filed on Aug. 30, 2013. The entire content of Japanese Patent Application No. 2013-180249 filed on Aug. 30, 2013 is incorporated herein by reference.

EXAMPLES

Hereinafter, the present invention is described in more detail with Examples. However, the present invention is not restricted to the following Examples.

Each of the mutant peptides produced in Examples below is represented by "domain-introduced mutation". The wild-type having no mutation introduced therein is represented by "domain-Wild". For example, the wild-type SpG-β1 domain shown as SEQ ID NO: 1 is represented by "β1-Wild", and the SpG-β1 domain mutant produced by introducing the mutation K13T is represented by "β1-K13T".

In the case of the mutant in which two kinds of mutations are simultaneously introduced, the mutations are written side by side with a slash between them. For example, the SpG-β1 domain mutant produced by introducing the mutations K13T and E19I is represented by "β1-K13T/E19I".

Further, a protein having a plurality of single domains connected thereto is represented such that the number of the connected domains and the letter d are written together after a period. For example, a protein in which two SpG-β1 domain mutants produced by introducing the mutations K13T and E19I are connected is represented by "β1-K13T/E19I.2d".

For example, in the case where a Cys residue (C) having a functional group for immobilization is introduced to the C-terminus in order to immobilize a protein on a water-insoluble base material, the first letter of the introduced amino acid is written after the letter d. For example, a protein in which two SpG-β1 domain mutants produced by introducing the mutations K13T and E19I are connected and Cys is added to the C-terminus is represented by "β1-K13T/E19I.2dC".

Example 1: Preparation of Various SpG-β1 Mutants (1) Preparation of Various SpG-β1 Mutant Expression Plasmids The preparation of expression plasmids will be described by taking the wild-type SpG-β1 as an example. A base sequence (SEQ ID NO: 3) encoding the peptide was constructed by reverse translation from the amino acid sequence of the wild-type SpG-β1 (SEQ ID NO: 1). Subsequently, the method for producing the expression plasmid is shown in FIG. 1. A DNA encoding the wild-type SpG-β1 was prepared so that two kinds of double-stranded DNAs (f1 and f2) having the same restriction enzyme site were connected together. The resultant DNA was introduced into the multiple cloning site of the expression vector. Actually, the encoding DNA preparation and the vector incorporation were simultaneously performed by three-fragment ligation for connecting two kinds of double-stranded DNAs and three kinds of double-stranded DNAs of the expression vector. In preparation of two kinds of double-stranded DNAs, two kinds of single-stranded oligo DNAs (f1-1/f1-2 or f2-1/f2-2) each containing about a 30-base complementary region were elongated by overlapping PCR, and a target double-stranded DNA was prepared. Specific experimental operation is as follows. Single-stranded oligo DNAs f1-1 (SEQ ID NO: 4)/f1-2 (SEQ ID NO: 5) were synthesized by outsourcing (manufactured by Sigma Genosys). The overlapping PCR reaction was performed using Pyrobest polymerase (manufactured by Takara Bio, Inc.). The PCR reaction product was subjected to agarose electrophoresis, and the target band was cut out. Thus, the extracted double stranded DNA was cleaved with the restriction enzymes BamHI and Eco52I (both available from Takara Bio, Inc.). Similarly, single-stranded oligo DNAs f2-1 (SEQ ID NO: 6)/f2-2 (SEQ ID NO: 7) were synthesized by outsourcing. The double-stranded DNA synthesized through the overlapping PCR reaction was extracted and cleaved with the restriction enzymes Eco52I and EcoRI (both available from Takara Bio, Inc.). Then, the two kinds of double-stranded DNAs were sub-cloned into the BamHI/EcoRI site in the multiple cloning site of the plasmid vector pGEX-6P-1 (GE Healthcare Bioscience). Ligation reaction for subcloning was performed using Ligation high (manufactured by TOYOBO CO., LTD.) in accordance with the protocol attached to the product.

Competent cells ("*Escherichia coli* HB101", manufactured by Takara Bio, Inc.) were transformed with the plasmid vector pGEX-6P-1 in accordance with the protocol attached to the competent cell products. The use of the plasmid vector pGEX-6P-1 allows for production of SpG-β1 to which glutathione-S-transferase (hereinafter, abbreviated as "GST") is fused. Then, the plasmid DNA was amplified and extracted using a plasmid purification kit ("Wizard Plus SV Minipreps DNA Purification System", manufactured by Promega) in accordance with the standard protocol attached to the kit. The base sequenues of the code DNAs of the expression plasmids were determined by using DNA sequencer ("3130x1 Genetic Analyzer", manufactured by Applied Biosystems). The sequencing PCR reaction was performed by using a gene analysis kit (BigDye Terminator v. 1.1 Cycle Sequencing Kit, manufactured by Applied Biosystems) and a DNA primer for sequencing the plasmid vector pGEX-6P-1 (manufactured by GE Healthcare Bioscience) in accordance with the attached protocol. The sequencing products were purified by using a plasmid purification kit (BigDye XTerminator Purification Kit, manufactured by Applied Biosystems) in accordance with the attached protocol and used for the base sequence analysis.

As for DNAs encoding various SpG-β1 mutants, a base sequence encoding the peptide was constructed by reverse translation from the desired amino acid sequence. Expression plasmids containing the code DNA and transformed cells were prepared in the same manner as described above. Currently, DNA of about 200 base pairs (enabling to encode a protein of 60 residues) can be totally synthesized by outsourcing (for example, manufactured by Eurogentec S.A.). Therefore, SEQ ID NOs. are described in the following table while corresponding to the amino acid sequences of the mutants to be encoded. Only the resulting final code DNA sequences are described in the sequence listing.

Further, the preparation of two-domain type expression plasmids will be described by taking the wild-type SpG-β1 as an example. The prepared code DNA site of the expression plasmid of single domain SpG-β1 was used as a template. A primer (SEQ ID NO: 8) having the BamHI recognition site added to the 5' side and a primer (SEQ ID NO: 9) having the HindIII recognition site added to the 3' side were used for PCR reaction to synthesize a double-stranded DNA (f-N). Similarly, a primer (SEQ ID NO: 10) having the HindIII recognition site added to the 5' side and a primer (SEQ ID NO: 11) having the EcoRI recognition site added to the 3' side were used for PCR reaction to synthesize a double-stranded DNA (f-C). Furthermore, in the case of the SpG-β1 mutant obtained by introducing a mutation to the 10th position, another primer (SEQ ID NO: 12) having the HindIII recognition site added to the 5' side was used. KOD-plus-polymerase (manufactured by TOYOBO CO., LTD.) was used for PCR reaction. The reaction product was subjected to agarose electrophoresis, and a target double-stranded DNA was extracted. f-N was cleaved with the restriction enzyme BamHI/HindIII, f-C was cleaved with HindIII/EcoRI, and plasmid vector pGEX-6P-1 was cleaved with the restriction enzyme BamHI/EcoRI. Expression plasmids were prepared by the same three fragment ligation procedure as described above. The subsequent transformation and confirmation of the base sequence were carried out by the same procedure as described above. Expression plasmids of various two-domain type SpG-β1 mutants were prepared by the same procedure.

(2) Preparation of Various SpG-β1 Mutants

Each of the transformed cells produced in the process (1) in which various SpG-β1 mutant genes were introduced was cultured in 2×YT medium containing ampicillin at 37° C. overnight. Each culture solution was inoculated in 2×YT medium containing about a 100-fold amount of ampicillin and cultured at 37° C. for about 2 hours. IPTG (isopropyl-1-thio-β-D-galactoside) was then added so as to have a final culture concentration of 0.1 mM, and each transformant was further cultured at 37° C. for 18 hours.

After the culture, bacterial cells were collected by centrifugation and re-suspended in 5 mL of PBS buffer. The cells were sonicated and centrifuged to separate a supernatant fraction (cell-free extract) and an insoluble fraction. A fusion peptide having GST added to the N-terminus is expressed by introducing the target gene to the multiple cloning site of the pGEX-6P-1 vector. In an SDS electrophoretic analysis of each of the fractions, a peptide band assumed to be induced by IPTG was detected at a position corresponding to a molecular weight of about not less than 25,000 for all of the various cell-free extracts obtained from the respective transformed cell cultures. Although the molecular weight was almost the same, the position of the band varied depending on the kind of the mutant.

The GST fusion peptide was roughly purified from each cell-free extract containing the GST fusion peptide by affinity chromatography using a GSTrap FF column (GE Healthcare Bioscience), which had an affinity for GST. Each cell-free extract was applied to the GSTrap FF column and the column was washed with a standard buffer (20 mM $NaH_2PO_4$—$Na_2HPO_4$, 150 mM NaCl, pH 7.4). Then, the target GST fusion peptide was eluted by using an elution buffer (50 mM Tris-HCl, 20 mM Glutathione, pH 8.0). The sample used for assay having the fused GST used in the following examples was a peptide solution obtained by concentrating this eluate through a centrifugal filter unit: Amicon (Merck Millipore Corporation) and replacing with a standard buffer.

When a gene is introduced into a multiple cloning site of the pGEX-6P-1 vector, an amino acid sequence that allows cleavage of GST with sequence-specific protease: PreScission Protease (manufactured by GE Healthcare Bioscience) is introduced between GST and a target protein. The GST cleavage reaction was performed by using PreScission Protease in accordance with the attached protocol. Each target peptide was purified from the GST-cleaved sample used for assay by gel filtration chromatography using a Superdex 75 10/300 GL column (manufactured by GE Healthcare Bioscience). Each reaction solution was added to the Superdex 75 10/300 GL column equilibrated with a standard buffer, and the target protein therein was separated and purified from the cleaved GST and PreScission Protease. In the two-domain type SpG-β1 mutants having a molecular weight close to that of GST, the eluted fraction was separated and purified by subjecting the eluted fraction to chromatography again in the same way. Further, all the peptide purification by chromatography using the column was performed by using an AKTAprime plus system (manufactured by GE Healthcare Biosceince). Furthermore, after the GST cleavage, the sequences of the proteins produced in Examples were the sequences having Gly-Pro-Leu-Gly-Ser derived from the vector pGEX-6P-1 to the N-terminal side.

Example 2

(1) Preparation of Fab Fragment Derived from IgG (IgG-Fab)

The Fab fragment was prepared by cleaving a humanized monoclonal IgG formulation as a starting material into a Fab fragment and an Fc fragment by papain, and separating and purifying only the Fab fragment. Shown herein is a method for preparing an IgG-Fab derived from anti-Her2 monoclonal antibody (generic name: Trastuzumab). Basically, another IgG-Fab such as an IgG-Fab derived from anti-TNFα monoclonal antibody (generic name: adalimumab) was also prepared in the same manner as described above.

Specifically, a humanized monoclonal IgG formulation (Herceptin, manufactured by Chugai Pharmaceutical Co., Ltd., in the case of anti-Her2 monoclonal antibody) was dissolved in a papain digestion buffer (0.1 M AcOH—AcONa, 2 mM EDTA, 1 mM cysteine, pH 5.5). Papain immobilized agarose: Papain Agarose from papaya latex (manufactured by Sigma) was added to the solution and the mixture was incubated at 37° C. for about 8 hours while being mixed with a rotator. The IgG-Fab was collected from flow-through fractions by affinity chromatography using a KanCapA column (manufactured by Kaneka Corporation). Thus, the IgG-Fab was separated and purified from the reaction solution (containing both the Fab fragment and the Fc fragment), which had been separated from the papain immobilized agarose. The separated IgG-Fab solution was purified by gel filtration chromatography using the Superdex 75 10/300 GL column (a standard buffer was used for equilibration and separation) to obtain an IgG-Fab solution. The protein purification by chromatography was performed by using an AKTAprime plus system in the same manner as in Example 1 (1).

(2) Analysis of Affinity of Various SpG-β1 Mutants for IgG-Fab

The affinity of each of the SpG-β1 mutants produced in Example 1 (2) for the IgG-Fab was analyzed by using a biosensor: Biacore 3000 using surface plasmon resonance principle (manufactured by GE Healthcare Bioscience). In this example, the IgG-Fab produced in Example 2 (1) was immobilized on a sensor chip and each peptide was added on the chip. The interaction between the IgG-Fab and the peptide was detected. The IgG-Fab was immobilized on the sensor chip CM5 by amine coupling using N-hydroxysuccinimide (NHS) and N-ethyl-N'-(3-dimethylaminopropyl) carbodiimide hydrochloride (EDC), and ethanolamine was used for blocking (all the sensor chips and the immobilization reagents were manufactured by GE Healthcare Bioscience). The IgG-Fab solution was about 10-fold diluted in an immobilization buffer (10 mM $CH_3COOH$—$CH_3COONa$, pH 4.5) and the IgG-Fab was immobilized on the sensor chip in accordance with the protocol attached to the Biacore 3000. Further, a reference cell to be used as a negative control was also prepared by immobilizing ethanolamine for another flow cell on the chip after activation by EDC/NHS. Various SpG-31 mutants were appropriately prepared at concentrations of 0.1 to 100 μM by using a running buffer (20 mM $NaH_2PO_4$—$Na_2HPO_4$, 150 mM NaCl, 0.005% P-20, pH 7.4). Each peptide solution was added on the sensor chip at a flow rate of 40 μL/minute for 60 seconds. A sensorgram of the binding reaction at 25° C. was sequentially plotted during the addition (binding phase, 60 seconds) and after the addition (dissociation phase, 60 seconds). After each sensorgram determination, the sensor chip was regenerated by adding 20 mM NaOH (for 30 seconds). This operation was performed for the purpose of removing the added peptides remaining on the sensor chip, and it was confirmed that the binding activity of the immobilized human IgG was almost completely recovered. The affinity constant to the human IgG ($K_A = k_{on}/k_{off}$) was calculated by performing fitting analysis on the obtained binding reaction sensorgram (the binding reaction sensorgram obtained by subtracting the binding reaction sensorgram of the reference cell) with the use of 1:1 binding model in a software BIA evaluation attached to the system. The results are shown in Table 1.

TABLE 1

| | SEQ ID NOs: | | anti-TNFα antibody-Fab | | | | anti-Her2antibody-Fab | | | |
| --- | --- | --- | --- | --- | --- | --- | --- | --- | --- | --- |
| | | | $k_{on}$ | $k_{off}$ | $K_A$ | | $k_{on}$ | $k_{off}$ | $K_A$ | |
| SpG mutant | amino acid sequence | base sequence | ×10$^4$ M$^{-1}$s$^{-1}$ | ×10$^{-2}$ s$^{-1}$ | ×10$^5$ M$^{-1}$ | Vs. Wild | ×10$^4$ M$^{-1}$s$^{-1}$ | ×10$^{-2}$ s$^{-1}$ | ×10$^5$ M$^{-1}$ | Vs. Wild |
| wild-type | 1 | 3 | 4.00 | 1.43 | 6.4 | — | 10.80 | 1.97 | 5.5 | — |
| K13T | 13 | 14 | 13.20 | 0.87 | 15.3 | 2.4 | 20.10 | 1.31 | 15.3 | 2.8 |
| K13T/E19I/F30L | 15 | 16 | 9.23 | 0.51 | 18.0 | 2.8 | 14.10 | 0.71 | 19.9 | 3.6 |
| K10R/K13T/K28Q/F30L/Q32R | 17 | 18 | 12.50 | 0.58 | 21.4 | 3.4 | 19.40 | 1.12 | 17.2 | 3.2 |
| K13T/E19I/V39I | 19 | 20 | 14.50 | 0.53 | 27.4 | 4.3 | 22.20 | 0.79 | 28.3 | 5.2 |
| K13T/F30L/D36G | 21 | 22 | 12.6 | 0.43 | 29.0 | 4.6 | 19.20 | 0.61 | 31.7 | 5.8 |

As shown in Table 1, in each of the mutants obtained by the present invention, it was confirmed that the binding constant for the IgG-Fab was improved as compared to the wild-type, and hence the binding force to the IgG-Fab was increased. The two kinds of the mutants have a similar tendency of improving the binding force to the IgG-Fab. Accordingly, the mutant obtained by the present invention is considered to bind to not the antigen binding region of IgG-Fab (a site whose sequence largely varies depending on the kind of antibody), but a common region in various antibodies, such as a constant region. Therefore, this is regarded as the result of supporting the high versatility of the mutant obtained by the present invention as an affinity ligand.

GST-SpGβ1-K13T.1d has a binding force to the IgG-Fab which is 2-fold or higher than GST-SpGβ1-Wild.1d. Thus, it can be said that the mutation K13T independently contributes to improvement in the binding force to the IgG-Fab. In addition, the mutation F30L is observed in a plurality of mutants. Among the mutations introduced into this mutant, the mutation F30L other than the mutation K13T may largely contribute to the improvement in the binding force to the IgG-Fab.

Example 3

The affinity of the SpG-β1 mutant for the IgG-Fab was measured in the same manner as in the experiment of Example 2. With respect to IgG-Fab, regarding the result observed in one type of IgG-Fab in the experiment of Example 2, the almost same tendency was found in another kind of IgG-Fab. The experiment was thus performed on just one type. The results are shown in Table 2.

have a close effect. Furthermore, the mutations F30L, E19I, and E19V are almost commonly observed in the mutant having not less than 5-fold binding force to the IgG-Fab. It can be said that these mutations highly contribute to the improvement in the binding force to the IgG-Fab. Particularly, it can be said that the mutations K13T and K13S concertedly contribute to the improvement in the binding force to the IgG-Fab.

In addition, the mutation Y33F is observed in a relatively large number of mutants and is considered to contribute to the improvement in the binding force to the IgG-Fab. In general, other mutations may contribute to the improvement in the binding force to the IgG-Fab. Further, in the case where the mutations at the 13th, 19th, 30th, and 33rd positions have not less than 80% sequence identity to

TABLE 2

|  | SEQ ID NOs: | | anti-TNFα antibody-Fab | | | |
|---|---|---|---|---|---|---|
| | | | $k_{on}$ | $k_{off}$ | $K_A$ | |
| SpG mutant | amino acid sequence | base sequence | $\times 10^4$ $M^{-1}s$ | $\times 10^{-2}$ $s^{-1}$ | $\times 10^5$ $M^{-1}$ | Vs. Wild |
| wild-type | 1 | 3 | 7.63 | 2.04 | 3.7 | — |
| K13T/F30L/D36G | 21 | 22 | 13.90 | 0.60 | 23.1 | 6.2 |
| K13T/E19I/F30L/Y33F/V39I/D47H | 23 | 24 | 7.94 | 0.39 | 20.6 | 5.5 |
| K13T/V21I/A23T/F30L/E42L | 25 | 26 | 8.50 | 0.59 | 14.4 | 3.9 |
| K13T/E19I/K28R/F30L/Y33F | 27 | 28 | 8.55 | 0.42 | 20.2 | 5.4 |
| K13S/E19I/F30L | 29 | 30 | 13.70 | 0.62 | 22.3 | 6.0 |
| K13T/E19I/A23D/V39L | 31 | 32 | 8.43 | 0.62 | 13.6 | 3.6 |
| K13T/E19I/K28N/F30L/D40V | 33 | 34 | 10.80 | 0.76 | 14.3 | 3.8 |
| K13T/E19I/E27D/F30L/K31R | 35 | 36 | 15.00 | 0.55 | 27.4 | 7.3 |
| K13T/E19I/V21N/K28I/F30L | 37 | 38 | 21.40 | 0.71 | 30.1 | 8.1 |
| K13T/E19I/K28N/E42K | 39 | 40 | 13.70 | 1.24 | 11.0 | 3.0 |
| K13T/E19I/Y33F/N35Y/V39L | 41 | 42 | 9.05 | 0.49 | 18.7 | 5.0 |
| K13T/E19I/F30L/D47N | 43 | 44 | 9.26 | 0.73 | 12.7 | 3.4 |
| K13T/E19I/A23T/F30L/Y33F/D47N/K50R | 45 | 46 | 12.00 | 0.46 | 26.3 | 7.0 |
| K13T/E19I/F30L/Y33F | 47 | 48 | 10.60 | 0.67 | 15.9 | 4.3 |
| K13T/E19I/A23T/T25M/F30L | 49 | 50 | 10.20 | 0.91 | 11.2 | 3.0 |
| K13T/V21A/F30L/Y33F/D40E | 51 | 52 | 13.90 | 0.78 | 17.8 | 4.8 |
| K13T/E19I/K28N/F30L/Y33F | 53 | 54 | 8.80 | 0.61 | 14.4 | 3.9 |
| K13T/E19I/V21D/T25M/F30L/Y33F/N35F/D47A | 55 | 56 | 10.40 | 0.30 | 34.7 | 9.3 |
| K13T/E19I/K28I/F30L/N35F | 57 | 58 | 8.80 | 0.63 | 14.0 | 3.7 |
| K13T/E19I/K28I/F30L/Y33F/E42Q/D47Y | 59 | 60 | 9.10 | 0.63 | 14.5 | 3.9 |
| K13T/E15Q/E19V/F30L/V39L | 61 | 62 | 8.98 | 0.63 | 14.2 | 3.8 |
| K13T/E15T/E19I/T25M/E27G/F30L/N35Y | 63 | 64 | 8.07 | 0.63 | 12.8 | 3.4 |
| K13T/E19I/F30L/D47A/K50E | 65 | 66 | 7.09 | 0.62 | 11.4 | 3.1 |
| K13T/T18A/E19V/F30L/Y33F | 67 | 68 | 9.36 | 0.33 | 28.5 | 7.6 |
| K10R/K13T/E15Q/K28R/F30L/D36G/E42V | 69 | 70 | 11.50 | 0.35 | 33.0 | 8.8 |
| K13T/K28I/F30L/D36G/V39I | 71 | 72 | 7.90 | 0.62 | 12.8 | 3.4 |
| K13T/D22N/A23T/T25S/F30L/A48T | 73 | 74 | 10.40 | 0.98 | 10.6 | 2.8 |
| K13T/E19I/V21D/K28I/F30L/K31R/D47H | 75 | 76 | 9.50 | 0.68 | 13.9 | 3.7 |
| K13T/E15Q/E19I/E27D/V39I/D47H | 77 | 78 | 12.40 | 0.67 | 18.5 | 4.9 |
| K13T/E19I/D22E/A24T/F30L/Y33F/D47G | 79 | 80 | 6.95 | 0.53 | 13.2 | 3.5 |
| K13S/E19V/F30L/Y33F | 81 | 82 | 9.84 | 0.64 | 15.4 | 4.1 |
| K13T/E19I/F30L/Y45F/D47Y | 83 | 84 | 9.77 | 0.70 | 13.9 | 3.7 |

As shown in the results in Table 2, GST-SpGβ1-K13T/F30L/D36G.1d showed about a 6-fold higher binding force to the IgG-Fab than GST-SpGβ1-Wild.1d. It can be said that this result is consistent with the fact that the binding force is about 5-fold in the experiment of Example 2. Further, it can be said naturally that this level of deviation in binding parameters between experiments is generated by the deterioration caused by repeatedly regenerating IgG-Fab on the sensor chip or the error caused by manual operation such as adjustment of concentration.

Further, the mutation K13T highly contributes to the improvement in the binding force to the IgG-Fab, similarly as described above. The mutation K13S is also considered to SpG-β1, they are generally considered to be capable of exhibiting the same function as SpG-β1.

Example 4

The affinity of the SpG-β1 mutant for the IgG-Fab was measured in the same manner as in the experiment of Example 3. In this experiment, the measurement was performed on the GST-cleaved type after the GST cleavage (Pep-). Further, not only one domain type (Pep.1d) but also one domain type with Cys at the C-terminus (Pep.1dC) and two domain type with Cys at the C-terminus (Pep.2dC) were used to perform the experiment. The results are shown in Table 3.

TABLE 3

| | | SEQ ID NOs: | | anti-TNFα antibody-Fab | | | |
|---|---|---|---|---|---|---|---|
| | | | | $k_{on}$ | $k_{off}$ | $K_A$ | |
| Construct | SpG mutant | amino acid sequence | base sequence | ×10⁴ $M^{-1}s$ | ×10⁻² $s^{-1}$ | ×10⁵ $M^{-1}$ | Vs. Wild |
| Pep.1d | wild-type | 1 | 3 | 3.88 | 27.0 | 1.44 | — |
| | K13T/E19I/V21D/T25M/F30L/Y33F/N35F/D47A | 55 | 56 | 10.9 | 2.57 | 42.4 | 29 |
| | K13T/T18A/E19I/V21A/K28I/F30L/Y33F/V39I | 85 | 86 | 11.1 | 2.07 | 53.4 | 37 |
| | K10R/K13T/T18A/E19I/V21D/T25M/F30L/Y33F/N35F/D47A | 87 | 88 | 13.8 | 1.17 | 119 | 83 |
| Pep.1dC | wild-type | 1 | 3 | 2.71 | 15.3 | 1.77 | — |
| | K13T/E19I/V21D/T25M/F30L/Y33F/N35F/D47A | 55 | 56 | 7.47 | 1.37 | 54.7 | 31 |
| | K13T/T18A/E19I/V21A/K28I/F30L/Y33F/V39I | 85 | 86 | 8.83 | 0.97 | 91.1 | 51 |
| | K10R/K13T/T18A/E19I/V21D/T25M/F30L/Y33F/N35F/D47A | 87 | 88 | 9.77 | 0.62 | 156 | 88 |
| Pep.2dC | wild-type | 1 | 3 | 1.92 | 5.68 | 3.38 | — |
| | K13T/E19I/V21D/T25M/F30L/Y33F/N35F/D47A | 55 | 56 | 5.57 | 0.58 | 96.8 | 29 |
| | K13T/T18A/E19I/V21A/K28I/F30L/Y33F/V39I | 85 | 86 | 6.39 | 0.62 | 102 | 30 |
| | K10R/K13T/T18A/E19I/V21D/T25M/F30L/Y33F/N35F/D47A | 87 | 88 | 11.7 | 0.14 | 856 | 253 |

As shown in the results in Table 3, the mutants obtained by the present invention had a significantly higher affinity for the IgG-Fab than the wild-type, similarly to those described above. Further, since Pep-SpGβ1-Wild.1d after the GST cleavage has a larger dissociation rate constant than GST-SpGβ1-Wild.1d, the binding constant is decreased. Taking into consideration the industrial production of the mutant as an affinity ligand, it is not particularly necessary to fuse GST. Accordingly, it can be said that the comparison under the conditions after the GST cleavage is close to the comparison under actual use conditions.

Pep-SpGβ1-K13T/E19I/V21D/T25M/F30L/Y33F/N35F/D47A.1d had a significantly higher affinity for the IgG-Fab than Pep-SpGβ1-Wild.1d, similarly to Example 3. The improvement in the affinity was represented by the binding constant and it reached a value close to 30-fold in the case of the Pep type after the GST cleavage.

Further, other mutants Pep-SpGβ1-K13T/T18A/E19I/V21A/K28I/F30L/Y33F/V39I.1d and Pep-SpGβ1-K10R/K13T/T18A/E19I/V21D/T25M/F30L/Y33F/N35F/D47A.1d obtained by the present invention also had a significantly higher affinity for the IgG-Fab than Pep-SpGβ1-Wild.1d.

Further, Pep-SpGβ1-K10R/K13T/T18A/E19I/V21D/T25M/F30L/Y33F/N35F/D47A.1d showed an 80-fold or higher binding constant than Pep-SpGβ1-Wild.1d. The affinity constant ($K_A$) was in the order of $10^7$ $M^{-1}$.

When compared to a one domain type construct with Cys at the C-terminus, similar results were also obtained. When compared to a two domain type construct with Cys at the C-terminus, similar results were also obtained; however, Pep-SpGβ1-K10R/K13T/T18A/E19I/V21D/T25M/F30L/Y33F/N35F/D47A.2dC showed a 200-fold or higher binding constant than Pep-SpGβ1-Wild.2dC.

Figure 2:
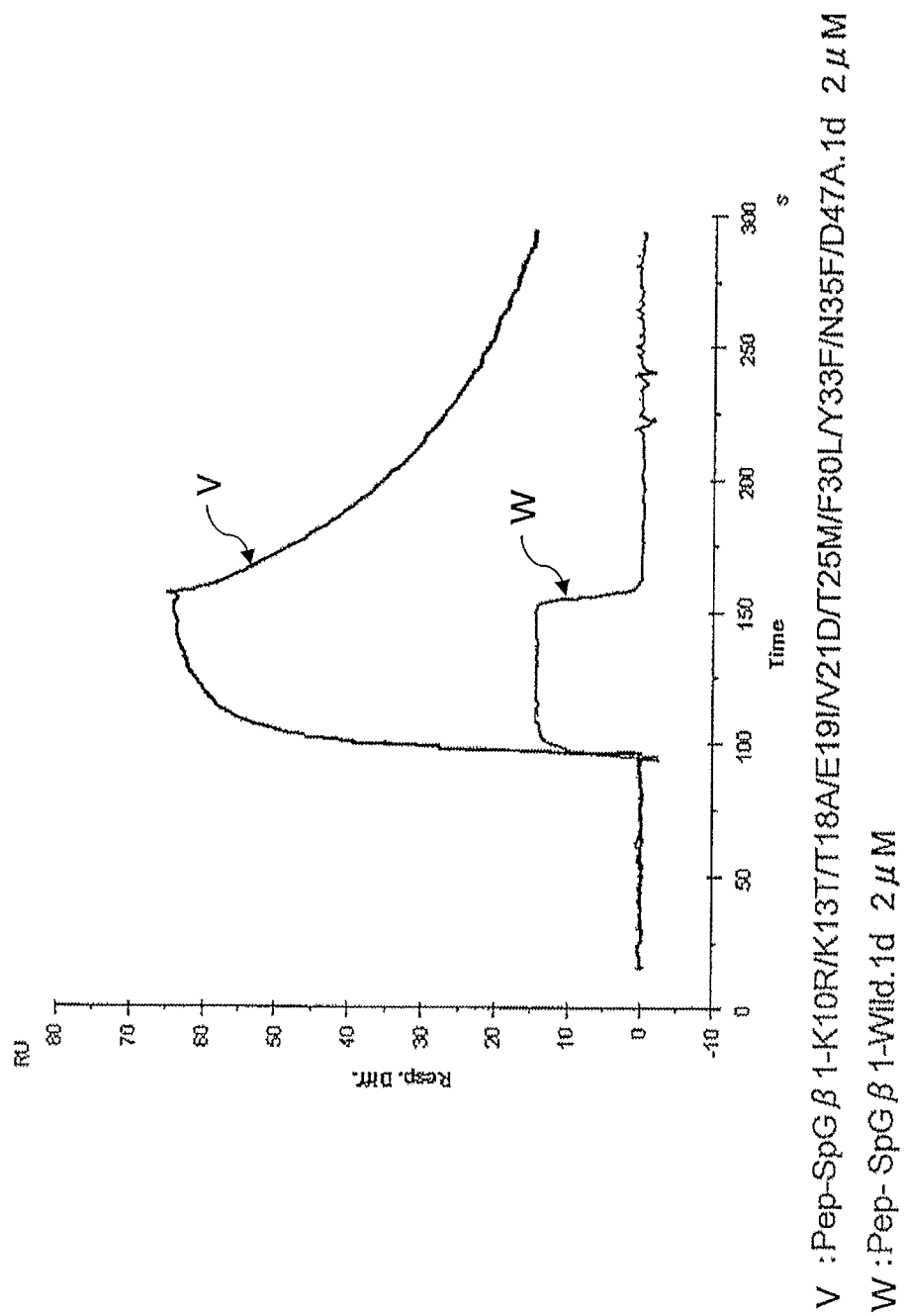
FIG. 2 is a sensorgram chart showing the binding reactions of W: wild-type SpG-β1 and V: mutant SpG-β1 obtained in the present invention with IgG-Fab of anti-TNFα monoclonal antibody.
Figure 3:
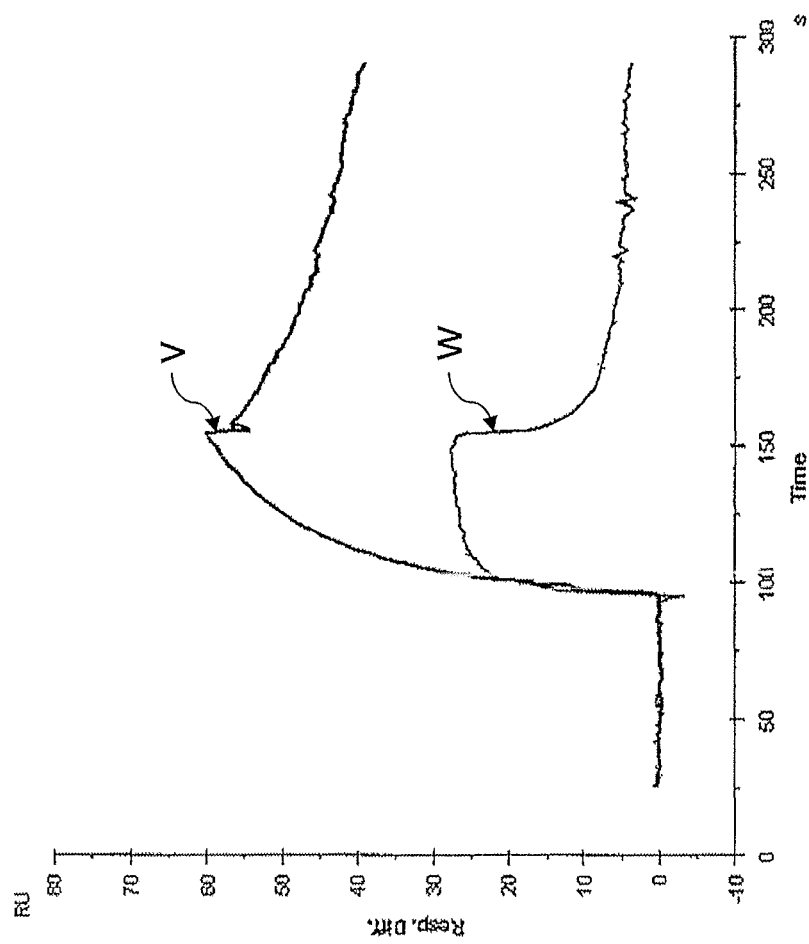
FIG. 3 is a sensorgram chart showing the binding reactions of W: wild-type SpG-β1 dimer and V: mutant SpG-β1 dimer obtained in the present invention with IgG-Fab of anti-TNFα monoclonal antibody.

As a reference, FIG. 2 shows a chart in which Biacore sensorgrams of the binding of wild-type SpG-β1 and K10R/K13T/T18A/E19I/V21D/T25M/F30L/Y33F/N35F/D47A at the same protein concentration (2 μM) to IgG-Fab of anti-TNFα monoclonal antibody are overlapped and compared by using the same type of construct (Pep.1d or Pep.2dC). FIG. 3 shows a chart in which Biacore sensorgrams of the binding of these dimers to IgG-Fab of anti-TNFα monoclonal antibody are overlapped and compared. As shown in FIGS. 2 and 3, it is understood that the mutant peptide according to the present invention, even in the case of a domain monomeric or dimeric peptide, has a higher binding ability to the Fab region than the wild-type SpG-β1.

In FIG. 2, the sensorgram of binding reaction of wild-type SpG-β1 is a typical box-shaped sensorgram which are observed when the binding rate constant is large (the dissociation of the interaction is rapid). The term "box-shaped" refers to a shape which is seen when the buildup of the signal (the binding phase) during the addition of sample is rapid, the binding is immediately in equilibrium (the signal is parallel to the baseline), and the signal (the dissociation phase) at the time of finishing the addition of sample decreases rapidly. As compared to the wild-type, the mutant SpG-β1 obtained by the present invention has a lower dissociation rate constant. Thus, the signal decrease at the time of finishing the addition of sample is represented by a gradual form. Therefore, it expected that the affinity separation matrix having the mutant SpG-β1 of the present invention immobilized thereon has a high retention performance for proteins containing the Fab region.

The invention claimed is:

1. A Fab region-binding peptide represented by any one of the following (1) to (3):

(1) a Fab region-binding peptide having an amino acid sequence of SEQ ID NO: 1 derived from the β1 domain of protein G with substitution of an amino acid residue at not less than one position selected from the 13th, 19th, 30th and 33rd positions, and having a higher binding force to the Fab region of immunoglobulin than that before introduction of the substitution, wherein the amino acid residue at the 13th position is substituted by Thr or Ser, the amino acid residue at the 30th position is substituted by Val, Leu or Ile, the amino acid residue at the 19th position is substituted by Val, Leu or Ile, the amino acid residue at the 33rd position is substituted by Phe;

(2) a Fab region-binding peptide having an amino acid sequence specified in the (1) with deletion, substitution and/or addition of not less than 1 and not more than 7 amino acid residues at a region other than the 13th, 19th, 30th and 33rd positions, and having a higher binding force to the Fab region of immunoglobulin than the peptide having the amino acid sequence of SEQ ID NO: 1;

wherein the position of deletion, substitution and/or addition of an amino acid residue is at least one position selected from the group consisting of the 2nd, 10th, 15th, 18th, 21st, 22nd, 23rd, 24th, 25th, 27th, 28th, 31st, 32nd, 35th, 36th, 39th, 40th, 42nd, 45th, 47th, 48th and 50th positions;

the amino acid residue at the 2nd position is substituted by Arg, the amino acid residue at the 10th position is substituted by Arg, the amino acid residue at the 15th position is substituted by Gln or Thr, the amino acid residue at the 18th position is substituted by Ala, the amino acid residue at the 21st position is substituted by Ile, Ala or Asp the amino acid residue at the 22nd position is substituted by Asn or Glu, the amino acid residue at the 23rd position is substituted by Thr or Asp, the amino acid residue at the 24th position is substituted by Thr, the amino acid residue at the 25th position is substituted by Ser or Met, the amino acid residue at the 27th position is substituted by Asp or Gly, the amino acid residue at the 28th position is substituted by Arg, Asn or Ile, the amino acid residue at the 31st position is substituted by Arg, the amino acid residue at the 32nd position is substituted by Arg, the amino acid residue at the 35th position is substituted by Phe or Tyr, the amino acid residue at the 36th position is substituted by Gly, the amino acid residue at the 39th position is substituted by Leu or Ile, the amino acid residue at the 40th position is substituted by Val or Glu, the amino acid residue at the 42nd position is substituted by Leu, Val or Gln, the amino acid residue at the 45th position is substituted by Phe, the amino acid residue at the 47th position is substituted by His, Asn, Ala, Gly or Tyr, the amino acid residue at the 48th position is substituted by Thr, and the amino acid residue at the 50th position is substituted by Arg or Glu, (3) a Fab region-binding peptide having an amino acid sequence having not less than 85% sequence identity to the amino acid sequence specified in the (1), and having a higher binding force to the Fab region of immunoglobulin than the peptide having the amino acid sequence of SEQ ID NO: 1, wherein the substituted amino acid residue at not less than 1 position selected from the 13th, 19th, 30th, and 33rd positions of the amino acid sequence specified in the (1) is not further mutated in the (3).

2. The Fab region-binding peptide according to claim 1, wherein the position of deletion, substitution and/or addition of an amino acid residue is at least one position selected from the 2nd, 10th, 15th, 18th, 21st, 22nd, 23rd, 24th, 25th, 27th, 28th, 31st, 32nd, 35th, 36th, 39th, 40th, 42nd, 45th, 47th and 48th positions of the amino acid sequence specified in the (2).

3. The Fab region-binding peptide according to claim 1, wherein the position of deletion, substitution and/or addition of an amino acid residue is an N-terminus and/or a C-terminus of the amino acid sequence specified in the (2).

4. The Fab region-binding peptide according to claim 1, wherein the sequence identity to the amino acid sequence specified in the (3) is not less than 95%.

5. A Fab region-binding peptide multimer, having not less than 2 domains wherein not less than 2 Fab region-binding peptides according to claim 1 are connected with one another.

6. An affinity separation matrix, wherein a Fab region-binding peptide according to claim 1 or a Fab region-binding peptide multimer according to claim 5 is immobilized on a water-insoluble carrier as a ligand.

7. A method for producing a Fab region-containing protein, comprising the steps of contacting the affinity separation matrix according to claim 6 with a liquid sample containing the Fab region-containing protein, and separating the Fab region-containing protein bound to the affinity separation matrix from the affinity separation matrix.

8. The Fab region-binding peptide according to claim 1, wherein the sequence identity to the amino acid sequence specified in the (3) is not less than 90%.

* * * * *

SEQUENCE LISTING

<160> NUMBER OF SEQ ID NOS: 88

<210> SEQ ID NO 1
<211> LENGTH: 56
<212> TYPE: PRT
<213> ORGANISM: Streptococcus sp. G148

<400> SEQUENCE: 1

Thr Thr Tyr Lys Leu Ile Leu Asn Gly Lys Thr Leu Lys Gly Glu Thr
1               5                   10                  15

Thr Thr Glu Ala Val Asp Ala Ala Thr Ala Glu Lys Val Phe Lys Gln
            20                  25                  30

Tyr Ala Asn Asp Asn Gly Val Asp Gly Glu Trp Thr Tyr Asp Asp Ala
            35                  40                  45

Thr Lys Thr Phe Thr Val Thr Glu
    50                  55

<210> SEQ ID NO 2
<211> LENGTH: 56
<212> TYPE: PRT
<213> ORGANISM: Streptococcus sp. G148

<400> SEQUENCE: 2

Thr Thr Tyr Lys Leu Val Ile Asn Gly Lys Thr Leu Lys Gly Glu Thr
1               5                   10                  15

Thr Thr Lys Ala Val Asp Ala Glu Thr Ala Glu Lys Ala Phe Lys Gln
            20                  25                  30

Tyr Ala Asn Asp Asn Gly Val Asp Gly Val Trp Thr Tyr Asp Asp Ala
            35                  40                  45

Thr Lys Thr Phe Thr Val Thr Glu
    50                  55

<210> SEQ ID NO 3
<211> LENGTH: 168
<212> TYPE: DNA
<213> ORGANISM: Artificial Sequence
<220> FEATURE:
<223> OTHER INFORMATION: DNA code

<400> SEQUENCE: 3
accacctaca aactgatcct gaacggtaag accctgaaag gtgaaaccac caccgaagct      60
gttgacgctg ctacggccga aaaagtgttc aaacagtacg ctaacgacaa cggtgtcgac     120
ggtgaatgga cctacgacga cgctaccaaa accttcacgg ttaccgaa                  168

<210> SEQ ID NO 4
<211> LENGTH: 60
<212> TYPE: DNA
<213> ORGANISM: Artificial Sequence
<220> FEATURE:
<223> OTHER INFORMATION: oligo DNA

<400> SEQUENCE: 4
cgtggatcca ccacctacaa actgatcctg aacggtaaga ccctgaaagg tgaaaccacc      60

<210> SEQ ID NO 5
<211> LENGTH: 60
<212> TYPE: DNA
<213> ORGANISM: Artificial Sequence
<220> FEATURE:
<223> OTHER INFORMATION: oligo DNA

<400> SEQUENCE: 5
ttcggccgta gcagcgtcaa cagcttcggt ggtggtttca cctttcaggg tcttaccgtt      60

<210> SEQ ID NO 6
<211> LENGTH: 70
<212> TYPE: DNA
<213> ORGANISM: Artificial Sequence
<220> FEATURE:
<223> OTHER INFORMATION: oligo DNA

<400> SEQUENCE: 6
ctacggccga aaaagtgttc aaacagtacg ctaacgacaa cggtgtcgac ggtgaatgga      60
cctacgacga                                                             70

<210> SEQ ID NO 7
<211> LENGTH: 70
<212> TYPE: DNA
<213> ORGANISM: Artificial Sequence
<220> FEATURE:
<223> OTHER INFORMATION: oligo DNA

<400> SEQUENCE: 7
cgatgaattc tattcggtaa ccgtgaaggt tttggtagcg tcgtcgtagg tccattcacc    60
gtcgacaccg                                                          70

<210> SEQ ID NO 8
<211> LENGTH: 23
<212> TYPE: DNA
<213> ORGANISM: Artificial Sequence
<220> FEATURE:
<223> OTHER INFORMATION: DNA primer

<400> SEQUENCE: 8
cctgggatcc accacctaca aac                                           23

<210> SEQ ID NO 9
<211> LENGTH: 32
<212> TYPE: DNA
<213> ORGANISM: Artificial Sequence
<220> FEATURE:
<223> OTHER INFORMATION: DNA primer

<400> SEQUENCE: 9
caggataagc ttgtaggtgg tttcggtaac cg                                 32

<210> SEQ ID NO 10
<211> LENGTH: 30
<212> TYPE: DNA
<213> ORGANISM: Artificial Sequence
<220> FEATURE:
<223> OTHER INFORMATION: DNA primer

<400> SEQUENCE: 10
acctacaagc ttatcctgaa cggtaagacc                                    30

<210> SEQ ID NO 11
<211> LENGTH: 23
<212> TYPE: DNA
<213> ORGANISM: Artificial Sequence
<220> FEATURE:
<223> OTHER INFORMATION: DNA primer

<400> SEQUENCE: 11
cgatgaattc tattcggtaa ccg                                           23

<210> SEQ ID NO 12
<211> LENGTH: 24
<212> TYPE: DNA
<213> ORGANISM: Artificial Sequence
<220> FEATURE:
<223> OTHER INFORMATION: DNA primer

<400> SEQUENCE: 12
acctacaagc ttatcctgaa cggt                                          24

<210> SEQ ID NO 13
<211> LENGTH: 56
<212> TYPE: PRT
<213> ORGANISM: Artificial Sequence
<220> FEATURE:
<223> OTHER INFORMATION: SpG mutant

<400> SEQUENCE: 13

Thr Thr Tyr Lys Leu Ile Leu Asn Gly Lys Thr Leu Thr Gly Glu Thr
1               5                   10                  15

Thr Thr Glu Ala Val Asp Ala Ala Thr Ala Glu Lys Val Phe Lys Gln
            20                  25                  30

Tyr Ala Asn Asp Asn Gly Val Asp Gly Glu Trp Thr Tyr Asp Asp Ala
        35                  40                  45

Thr Lys Thr Phe Thr Val Thr Glu
    50                  55

<210> SEQ ID NO 14
<211> LENGTH: 168
<212> TYPE: DNA
<213> ORGANISM: Artificial Sequence
<220> FEATURE:
<223> OTHER INFORMATION: DNA code

<400> SEQUENCE: 14
accacctaca aactgatcct gaacggtaag accctgacag gtgaaaccac caccgaagct      60
gttgacgctg ctacggccga aaaagtgttc aaacagtacg ctaacgacaa cggtgtcgac     120
ggtgaatgga cctacgacga cgctaccaaa accttcacgg ttaccgaa                  168

<210> SEQ ID NO 15
<211> LENGTH: 56
<212> TYPE: PRT
<213> ORGANISM: Artificial Sequence
<220> FEATURE:
<223> OTHER INFORMATION: SpG mutant

<400> SEQUENCE: 15

Thr Thr Tyr Lys Leu Ile Leu Asn Gly Lys Thr Leu Thr Gly Glu Thr
1               5                   10                  15

Thr Thr Ile Ala Val Asp Ala Ala Thr Ala Glu Lys Val Leu Lys Gln
            20                  25                  30

Tyr Ala Asn Asp Asn Gly Val Asp Gly Glu Trp Thr Tyr Asp Asp Ala
        35                  40                  45

Thr Lys Thr Phe Thr Val Thr Glu
    50                  55

<210> SEQ ID NO 16
<211> LENGTH: 168
<212> TYPE: DNA
<213> ORGANISM: Artificial Sequence
<220> FEATURE:
<223> OTHER INFORMATION: DNA code

<400> SEQUENCE: 16
accacctaca aactgatcct gaacgggaag accctgacag gtgaaaccac cacaatagca      60
gttgacgctg ctacggccga aaaagtgttg aaacagtacg ctaacgacaa cggtgtcgac     120
ggcgaatgga cctacgacga cgctaccaaa accttcacgg ttaccgaa                  168

<210> SEQ ID NO 17
<211> LENGTH: 56
<212> TYPE: PRT
<213> ORGANISM: Artificial Sequence
<220> FEATURE:
<223> OTHER INFORMATION: SpG mutant

<400> SEQUENCE: 17

Thr Thr Tyr Lys Leu Ile Leu Asn Gly Arg Thr Leu Thr Gly Glu Thr
1               5                   10                  15

Thr Thr Glu Ala Val Asp Ala Ala Thr Ala Glu Gln Val Leu Lys Arg
            20                  25                  30

Tyr Ala Asn Asp Asn Gly Val Asp Gly Glu Trp Thr Tyr Asp Asp Ala
        35                  40                  45

Thr Lys Thr Phe Thr Val Thr Glu
    50                  55

<210> SEQ ID NO 18
<211> LENGTH: 168
<212> TYPE: DNA
<213> ORGANISM: Artificial Sequence
<220> FEATURE:
<223> OTHER INFORMATION: DNA code

<400> SEQUENCE: 18
accacctaca aactgatcct gaacggtagg accctgacag gtgaaaccac caccgaagct    60
gttgacgctg ctactgccga acaagtgctc aaacggtacg ctaacgacaa cggtgtcgac   120
ggtgaatgga cctacgacga cgctaccaaa accttcacgg ttaccgag                168

<210> SEQ ID NO 19
<211> LENGTH: 56
<212> TYPE: PRT
<213> ORGANISM: Artificial Sequence
<220> FEATURE:
<223> OTHER INFORMATION: SpG mutant

<400> SEQUENCE: 19

Thr Thr Tyr Lys Leu Ile Leu Asn Gly Lys Thr Leu Thr Gly Glu Thr
1               5                   10                  15

Thr Thr Ile Ala Val Asp Ala Ala Thr Ala Glu Lys Val Phe Lys Gln
            20                  25                  30

Tyr Ala Asn Asp Asn Gly Ile Asp Gly Glu Trp Thr Tyr Asp Asp Ala
        35                  40                  45

Thr Lys Thr Phe Thr Val Thr Glu
    50                  55

<210> SEQ ID NO 20
<211> LENGTH: 168
<212> TYPE: DNA
<213> ORGANISM: Artificial Sequence
<220> FEATURE:
<223> OTHER INFORMATION: DNA code

<400> SEQUENCE: 20
accacctaca aactaatcct gaacggaaag accctgacag gtgaaaccac caccatagct    60
gttgacgctg ctacggccga aaaagtgttc aaacagtacg ctaacgacaa cggtatcgac   120
ggtgaatgga cctacgacga cgctaccaaa accttcacgg ttaccgag                168

<210> SEQ ID NO 21
<211> LENGTH: 56
<212> TYPE: PRT
<213> ORGANISM: Artificial Sequence
<220> FEATURE:
<223> OTHER INFORMATION: SpG mutant

<400> SEQUENCE: 21

Thr Thr Tyr Lys Leu Ile Leu Asn Gly Lys Thr Leu Thr Gly Glu Thr
1               5                   10                  15

Thr Thr Glu Ala Val Asp Ala Ala Thr Ala Glu Lys Val Leu Lys Gln
            20                  25                  30

Tyr Ala Asn Gly Asn Gly Val Asp Gly Glu Trp Thr Tyr Asp Asp Ala
        35                  40                  45

Thr Lys Thr Phe Thr Val Thr Glu
    50                  55

<210> SEQ ID NO 22
<211> LENGTH: 168
<212> TYPE: DNA
<213> ORGANISM: Artificial Sequence
<220> FEATURE:
<223> OTHER INFORMATION: DNA code

<400> SEQUENCE: 22
accacctaca aactgatcct gaacggtaag accctgacag gtgaaaccac caccgaagct      60
gttgacgctg ctacggccga aaaagtgctc aaacagtacg ctaacggcaa cggtgtcgac     120
ggtgaatgga cctacgacga cgctaccaaa accttcacgg ttaccgag                  168

<210> SEQ ID NO 23
<211> LENGTH: 56
<212> TYPE: PRT
<213> ORGANISM: Artificial Sequence
<220> FEATURE:
<223> OTHER INFORMATION: SpG mutant

<400> SEQUENCE: 23

Thr Thr Tyr Lys Leu Ile Leu Asn Gly Lys Thr Leu Thr Gly Glu Thr
1               5                   10                  15

Thr Thr Ile Ala Val Asp Ala Ala Thr Ala Glu Lys Val Leu Lys Gln
            20                  25                  30

Phe Ala Asn Asp Asn Gly Ile Asp Gly Glu Trp Thr Tyr Asp His Ala
        35                  40                  45

Thr Lys Thr Phe Thr Val Thr Glu
    50                  55

<210> SEQ ID NO 24
<211> LENGTH: 168
<212> TYPE: DNA
<213> ORGANISM: Artificial Sequence
<220> FEATURE:
<223> OTHER INFORMATION: DNA code

<400> SEQUENCE: 24
accacctaca aactgatcct gaacggcaag accctgacag gtgaaaccac caccatagct      60
gttgacgctg ctactgccga aaaagtgctg aaacagttcg ctaacgacaa cggtatcgac     120
ggtgaatgga cctacgacca cgctaccaaa accttcacgg ttaccgaa                  168

<210> SEQ ID NO 25
<211> LENGTH: 56
<212> TYPE: PRT
<213> ORGANISM: Artificial Sequence
<220> FEATURE:
<223> OTHER INFORMATION: SpG mutant

<400> SEQUENCE: 25

Thr Thr Tyr Lys Leu Ile Leu Asn Gly Lys Thr Leu Thr Gly Glu Thr
1               5                   10                  15
Thr Thr Glu Ala Ile Asp Thr Ala Glu Lys Val Leu Lys Gln
            20                  25                  30
Tyr Ala Asn Asp Asn Gly Val Asp Gly Leu Trp Thr Tyr Asp Asp Ala
        35                  40                  45
Thr Lys Thr Phe Thr Val Thr Glu
    50                  55

<210> SEQ ID NO 26
<211> LENGTH: 168
<212> TYPE: DNA
<213> ORGANISM: Artificial Sequence
<220> FEATURE:
<223> OTHER INFORMATION: DNA code

<400> SEQUENCE: 26
accacctaca aactgatcct gaacggcaag accctgacag gtgaaaccac caccgaagct    60
attgacactg ctactgccga aaaagtgctc aaacagtacg ctaacgacaa cggagtcgac   120
ggtctatgga cctacgacga cgctaccaaa accttcacgg ttaccgaa              168

<210> SEQ ID NO 27
<211> LENGTH: 56
<212> TYPE: PRT
<213> ORGANISM: Artificial Sequence
<220> FEATURE:
<223> OTHER INFORMATION: SpG mutant

<400> SEQUENCE: 27

Thr Thr Tyr Lys Leu Ile Leu Asn Gly Lys Thr Leu Thr Gly Glu Thr
1               5                   10                  15
Thr Thr Ile Ala Val Asp Ala Ala Thr Ala Glu Arg Val Leu Lys Gln
            20                  25                  30
Phe Ala Asn Asp Asn Gly Val Asp Gly Glu Trp Thr Tyr Asp Asp Ala
        35                  40                  45
Thr Lys Thr Phe Thr Val Thr Glu
    50                  55

<210> SEQ ID NO 28
<211> LENGTH: 168
<212> TYPE: DNA
<213> ORGANISM: Artificial Sequence
<220> FEATURE:
<223> OTHER INFORMATION: DNA code

<400> SEQUENCE: 28
accacctaca aactgatcct gaacggcaag accctgacag gtgaaaccac caccatagct    60
gttgacgctg ctacggccga aagagtgctc aaacagttcg ctaacgacaa cggtgtcgac   120
ggtgaatgga cctacgacga cgctaccaaa accttcacgg ttaccgaa              168

<210> SEQ ID NO 29
<211> LENGTH: 56
<212> TYPE: PRT
<213> ORGANISM: Artificial Sequence
<220> FEATURE:
<223> OTHER INFORMATION: SpG mutant

<400> SEQUENCE: 29

Thr Thr Tyr Lys Leu Ile Leu Asn Gly Lys Thr Leu Ser Gly Glu Thr
1               5                   10                  15

Thr Thr Ile Ala Val Asp Ala Ala Thr Ala Glu Lys Val Leu Lys Gln
            20                  25                  30

Tyr Ala Asn Asp Asn Gly Val Asp Gly Glu Trp Thr Tyr Asp Asp Ala
        35                  40                  45

Thr Lys Thr Phe Thr Val Thr Glu
    50                  55

<210> SEQ ID NO 30
<211> LENGTH: 168
<212> TYPE: DNA
<213> ORGANISM: Artificial Sequence
<220> FEATURE:
<223> OTHER INFORMATION: DNA code

<400> SEQUENCE: 30
accacctaca aactgatcct gaacggcaag accctgtcag gtgaaaccac caccatagct      60
gttgacgctg ctacggccga aaaagtgctc aaacagtacg ctaacgacaa cggtgtcgac     120
ggtgaatgga cctatgacga cgctaccaaa accttcacgg ttaccgaa                  168

<210> SEQ ID NO 31
<211> LENGTH: 56
<212> TYPE: PRT
<213> ORGANISM: Artificial Sequence
<220> FEATURE:
<223> OTHER INFORMATION: SpG mutant

<400> SEQUENCE: 31

Thr Thr Tyr Lys Leu Ile Leu Asn Gly Lys Thr Leu Thr Gly Glu Thr
1               5                   10                  15

Thr Thr Ile Ala Val Asp Asp Ala Thr Ala Glu Lys Val Phe Lys Gln
            20                  25                  30

Tyr Ala Asn Asp Asn Gly Leu Asp Gly Glu Trp Thr Tyr Asp Asp Ala
        35                  40                  45

Thr Lys Thr Phe Thr Val Thr Glu
    50                  55

<210> SEQ ID NO 32
<211> LENGTH: 168
<212> TYPE: DNA
<213> ORGANISM: Artificial Sequence
<220> FEATURE:
<223> OTHER INFORMATION: DNA code

<400> SEQUENCE: 32
accacctaca aactgatcct gaacggcaag accctgacag gtgaaaccac caccatagca      60
gttgacgatg ctacggccga gaaagtgttc aaacagtacg ctaacgacaa cggtctcgac     120
ggtgaatgga cctacgacga cgctaccaaa accttcacgg ttaccgaa                  168

<210> SEQ ID NO 33
<211> LENGTH: 56
<212> TYPE: PRT
<213> ORGANISM: Artificial Sequence
<220> FEATURE:
<223> OTHER INFORMATION: SpG mutant

<400> SEQUENCE: 33

Thr Thr Tyr Lys Leu Ile Leu Asn Gly Lys Thr Leu Thr Gly Glu Thr
1               5                   10                  15

Thr Thr Ile Ala Val Asp Ala Ala Thr Ala Glu Asn Val Leu Lys Gln
            20                  25                  30

Tyr Ala Asn Asp Asn Gly Val Val Gly Glu Trp Thr Tyr Asp Asp Ala
        35                  40                  45

Thr Lys Thr Phe Thr Val Thr Glu
    50                  55

<210> SEQ ID NO 34
<211> LENGTH: 168
<212> TYPE: DNA
<213> ORGANISM: Artificial Sequence
<220> FEATURE:
<223> OTHER INFORMATION: DNA code

<400> SEQUENCE: 34
accacctaca aactgatcct gaacggcaag accctgacag gcgaaaccac caccatagct     60
gttgacgctg ctacggccga aaatgtgctc aaacagtacg ctaacgacaa cggtgtcgtc    120
ggtgaatgga cctacgacga tgctaccaaa accttcacgg ttaccgaa                 168

<210> SEQ ID NO 35
<211> LENGTH: 56
<212> TYPE: PRT
<213> ORGANISM: Artificial Sequence
<220> FEATURE:
<223> OTHER INFORMATION: SpG mutant

<400> SEQUENCE: 35

Thr Thr Tyr Lys Leu Ile Leu Asn Gly Lys Thr Leu Thr Gly Glu Thr
1               5                   10                  15

Thr Thr Ile Ala Val Asp Ala Ala Thr Ala Asp Lys Val Leu Arg Gln
            20                  25                  30

Tyr Ala Asn Asp Asn Gly Val Asp Gly Glu Trp Thr Tyr Asp Asp Ala
        35                  40                  45

Thr Lys Thr Phe Thr Val Thr Glu
    50                  55

<210> SEQ ID NO 36
<211> LENGTH: 168
<212> TYPE: DNA
<213> ORGANISM: Artificial Sequence
<220> FEATURE:
<223> OTHER INFORMATION: DNA code

<400> SEQUENCE: 36
accacctaca aactgatcct gaacggcaag accctgacag gtgaaaccac caccatagct     60
gttgacgctg ctacggccga caaagtgctc agacagtacg ctaacgacaa tggtgtcgac    120
ggtgaatgga cctacgacga cgctaccaaa accttcacgg ttaccgaa                 168

<210> SEQ ID NO 37
<211> LENGTH: 56
<212> TYPE: PRT
<213> ORGANISM: Artificial Sequence
<220> FEATURE:
<223> OTHER INFORMATION: SpG mutant

<400> SEQUENCE: 37

Thr Thr Tyr Lys Leu Ile Leu Asn Gly Lys Thr Leu Thr Gly Glu Thr
1               5                   10                  15

Thr Thr Ile Ala Asn Asp Ala Ala Thr Ala Glu Ile Val Leu Lys Gln
            20                  25                  30

Tyr Ala Asn Asp Asn Gly Val Asp Gly Glu Trp Thr Tyr Asp Asp Ala
        35                  40                  45

Thr Lys Thr Phe Thr Val Thr Glu
    50                  55

<210> SEQ ID NO 38
<211> LENGTH: 168
<212> TYPE: DNA
<213> ORGANISM: Artificial Sequence
<220> FEATURE:
<223> OTHER INFORMATION: DNA code

<400> SEQUENCE: 38
accacctaca aactgatcct gaacggcaaa accctgacag gtgaaaccac caccatagct     60
aatgacgctg ctaccgccga aatagtgctc aaacagtacg ctaacgacaa cggtgtcgac    120
ggagaatgga cctacgacga cgctaccaaa accttcacgg ttaccgaa                 168

<210> SEQ ID NO 39
<211> LENGTH: 56
<212> TYPE: PRT
<213> ORGANISM: Artificial Sequence
<220> FEATURE:
<223> OTHER INFORMATION: SpG mutant

<400> SEQUENCE: 39

Thr Thr Tyr Lys Leu Ile Leu Asn Gly Lys Thr Leu Thr Gly Glu Thr
1               5                   10                  15

Thr Thr Ile Ala Val Asp Ala Ala Thr Ala Glu Asn Val Phe Lys Gln
            20                  25                  30

Tyr Ala Asn Asp Asn Gly Val Asp Gly Lys Trp Thr Tyr Asp Asp Ala
        35                  40                  45

Thr Lys Thr Phe Thr Val Thr Glu
    50                  55

<210> SEQ ID NO 40
<211> LENGTH: 168
<212> TYPE: DNA
<213> ORGANISM: Artificial Sequence
<220> FEATURE:
<223> OTHER INFORMATION: DNA code

<400> SEQUENCE: 40
accacctaca aactgatcct gaacggcaag accctgacag gtgaaaccac aaccatagct     60
gtcgacgccg ctacggccga aaatgtgttc aaacagtacg ctaacgacaa cggcgtcgac    120
ggtaaatgga cctacgacga tgctaccaaa accttcacgg ttaccgaa                 168

<210> SEQ ID NO 41
<211> LENGTH: 56
<212> TYPE: PRT
<213> ORGANISM: Artificial Sequence
<220> FEATURE:
<223> OTHER INFORMATION: SpG mutant

<400> SEQUENCE: 41

Thr Thr Tyr Lys Leu Ile Leu Asn Gly Lys Thr Leu Thr Gly Glu Thr
1               5                   10                  15

Thr Thr Ile Ala Val Asp Ala Ala Thr Ala Glu Lys Val Phe Lys Gln
            20                  25                  30

Phe Ala Tyr Asp Asn Gly Leu Asp Gly Glu Trp Thr Tyr Asp Asp Ala
        35                  40                  45

Thr Lys Thr Phe Thr Val Thr Glu
    50                  55

<210> SEQ ID NO 42
<211> LENGTH: 168
<212> TYPE: DNA
<213> ORGANISM: Artificial Sequence
<220> FEATURE:
<223> OTHER INFORMATION: DNA code

<400> SEQUENCE: 42
accacctaca aactgatcct gaacggcaag accctgacag gtgaaaccac caccatagct        60
gttgacgccg ctacggccga aaaagtgttc aaacagttcg cttacgacaa cggtctcgac       120
ggtgaatgga cctacgacga cgctaccaaa accttcacgg ttaccgaa                    168

<210> SEQ ID NO 43
<211> LENGTH: 56
<212> TYPE: PRT
<213> ORGANISM: Artificial Sequence
<220> FEATURE:
<223> OTHER INFORMATION: SpG mutant

<400> SEQUENCE: 43

Thr Thr Tyr Lys Leu Ile Leu Asn Gly Lys Thr Leu Thr Gly Glu Thr
1               5                   10                  15

Thr Thr Ile Ala Val Asp Ala Ala Thr Ala Glu Lys Val Leu Lys Gln
            20                  25                  30

Tyr Ala Asn Asp Asn Gly Val Asp Gly Glu Trp Thr Tyr Asp Asn Ala
        35                  40                  45

Thr Lys Thr Phe Thr Val Thr Glu
    50                  55

<210> SEQ ID NO 44
<211> LENGTH: 168
<212> TYPE: DNA
<213> ORGANISM: Artificial Sequence
<220> FEATURE:
<223> OTHER INFORMATION: DNA code

<400> SEQUENCE: 44
accacctaca aactgatcct gaacggcaag accctgacag gtgaaaccac caccatagct        60
gtggacgctg ctacggccga gaaagtgctc aaacagtacg ctaacgacaa cggtgtcgac       120
ggtgaatgga cctacgacaa cgctaccaaa accttcacgg ttaccgaa                    168

<210> SEQ ID NO 45
<211> LENGTH: 56
<212> TYPE: PRT
<213> ORGANISM: Artificial Sequence
<220> FEATURE:
<223> OTHER INFORMATION: SpG mutant

<400> SEQUENCE: 45

Thr Thr Tyr Lys Leu Ile Leu Asn Gly Lys Thr Leu Thr Gly Glu Thr
1               5                   10                  15

Thr Thr Ile Ala Val Asp Thr Ala Ala Glu Lys Val Leu Lys Gln
            20                  25                  30

Phe Ala Asn Asp Asn Gly Val Asp Gly Glu Trp Thr Tyr Asp Asn Ala
        35                  40                  45

Thr Arg Thr Phe Thr Val Thr Glu
    50                  55

<210> SEQ ID NO 46
<211> LENGTH: 168
<212> TYPE: DNA
<213> ORGANISM: Artificial Sequence
<220> FEATURE:
<223> OTHER INFORMATION: DNA code

<400> SEQUENCE: 46
accacctaca aactgatcct gaacggcaag accctgacag gtgaaaccac caccatagct      60
gttgacactg ctacggccga aaaagtgtta aaacagttcg ctaacgacaa cggtgtcgac     120
ggtgaatgga cctacgacaa cgctaccaga accttcacgg ttaccgaa                  168

<210> SEQ ID NO 47
<211> LENGTH: 56
<212> TYPE: PRT
<213> ORGANISM: Artificial Sequence
<220> FEATURE:
<223> OTHER INFORMATION: SpG mutant

<400> SEQUENCE: 47

Thr Thr Tyr Lys Leu Ile Leu Asn Gly Lys Thr Leu Thr Gly Glu Thr
1               5                   10                  15

Thr Thr Ile Ala Val Asp Ala Ala Thr Ala Glu Lys Val Leu Lys Gln
            20                  25                  30

Phe Ala Asn Asp Asn Gly Val Asp Gly Glu Trp Thr Tyr Asp Asp Ala
        35                  40                  45

Thr Lys Thr Phe Thr Val Thr Glu
    50                  55

<210> SEQ ID NO 48
<211> LENGTH: 168
<212> TYPE: DNA
<213> ORGANISM: Artificial Sequence
<220> FEATURE:
<223> OTHER INFORMATION: DNA code

<400> SEQUENCE: 48
accacctaca aactgatcct gaacggcaag accctgacag gtgaaaccac caccatagct      60
gttgacgctg ctacggccga aaaagtgctc aaacagttcg ctaacgacaa cggcgtcgac     120
ggtgaatgga cctacgacga cgctaccaaa accttcacgg ttaccgaa                  168

<210> SEQ ID NO 49
<211> LENGTH: 56
<212> TYPE: PRT
<213> ORGANISM: Artificial Sequence
<220> FEATURE:
<223> OTHER INFORMATION: SpG mutant

<400> SEQUENCE: 49

Thr Thr Tyr Lys Leu Ile Leu Asn Gly Lys Thr Leu Thr Gly Glu Thr
1               5                   10                  15

Thr Thr Ile Ala Val Asp Thr Ala Met Ala Glu Lys Val Leu Lys Gln
            20                  25                  30

Tyr Ala Asn Asp Asn Gly Val Asp Gly Glu Trp Thr Tyr Asp Asp Ala
        35                  40                  45

Thr Lys Thr Phe Thr Val Thr Glu
    50                  55

<210> SEQ ID NO 50
<211> LENGTH: 168
<212> TYPE: DNA
<213> ORGANISM: Artificial Sequence
<220> FEATURE:
<223> OTHER INFORMATION: DNA code

<400> SEQUENCE: 50
accacctaca aactgatcct gaacggcaag accctgacag gtgaaaccac caccatagca      60
gttgacactg ctatggccga gaaagtgctc aaacagtacg ctaacgacaa cggcgtcgac     120
ggtgaatgga cctacgacga tgctaccaaa accttcacgg ttaccgaa                  168

<210> SEQ ID NO 51
<211> LENGTH: 56
<212> TYPE: PRT
<213> ORGANISM: Artificial Sequence
<220> FEATURE:
<223> OTHER INFORMATION: SpG mutant

<400> SEQUENCE: 51

Thr Thr Tyr Lys Leu Ile Leu Asn Gly Lys Thr Leu Thr Gly Glu Thr
1               5                   10                  15

Thr Thr Glu Ala Ala Asp Ala Ala Thr Ala Glu Lys Val Leu Lys Gln
            20                  25                  30

Phe Ala Asn Asp Asn Gly Val Glu Gly Glu Trp Thr Tyr Asp Asp Ala
        35                  40                  45

Thr Lys Thr Phe Thr Val Thr Glu
    50                  55

<210> SEQ ID NO 52
<211> LENGTH: 168
<212> TYPE: DNA
<213> ORGANISM: Artificial Sequence
<220> FEATURE:
<223> OTHER INFORMATION: DNA code

<400> SEQUENCE: 52
accacctaca aactgatcct gaacggcaag accctgacag gtgaaaccac caccgaagct      60
gctgacgctg ctacggccga aaaagtgctc aaacagttcg ctaacgacaa cggtgtcgag     120
ggtgaatgga cctacgacga cgctaccaaa accttcacgg ttaccgaa                  168

<210> SEQ ID NO 53
<211> LENGTH: 56
<212> TYPE: PRT
<213> ORGANISM: Artificial Sequence
<220> FEATURE:
<223> OTHER INFORMATION: SpG mutant

<400> SEQUENCE: 53

Thr Thr Tyr Lys Leu Ile Leu Asn Gly Lys Thr Leu Thr Gly Glu Thr
1               5                   10                  15

Thr Thr Ile Ala Val Asp Ala Ala Thr Ala Glu Asn Val Leu Lys Gln
            20                  25                  30

Phe Ala Asn Asp Asn Gly Val Asp Gly Glu Trp Thr Tyr Asp Asp Ala
        35                  40                  45

Thr Lys Thr Phe Thr Val Thr Glu
    50                  55

<210> SEQ ID NO 54
<211> LENGTH: 168
<212> TYPE: DNA
<213> ORGANISM: Artificial Sequence
<220> FEATURE:
<223> OTHER INFORMATION: DNA code

<400> SEQUENCE: 54
accacctaca aactgatcct gaacggcaag accctgacag gtgaaaccac caccatagct      60
gttgacgctg ctacggccga aaatgtgctc aaacagttcg ctaacgacaa cggtgtcgac     120
ggtgaatgga cctacgacga cgctaccaaa accttcacgg ttaccgaa                  168

<210> SEQ ID NO 55
<211> LENGTH: 56
<212> TYPE: PRT
<213> ORGANISM: Artificial Sequence
<220> FEATURE:
<223> OTHER INFORMATION: SpG mutant

<400> SEQUENCE: 55

Thr Thr Tyr Lys Leu Ile Leu Asn Gly Lys Thr Leu Thr Gly Glu Thr
1               5                   10                  15

Thr Thr Ile Ala Asp Asp Ala Ala Met Ala Glu Lys Val Leu Lys Gln
            20                  25                  30

Phe Ala Phe Asp Asn Gly Val Asp Gly Glu Trp Thr Tyr Asp Ala Ala
        35                  40                  45

Thr Lys Thr Phe Thr Val Thr Glu
    50                  55

<210> SEQ ID NO 56
<211> LENGTH: 168
<212> TYPE: DNA
<213> ORGANISM: Artificial Sequence
<220> FEATURE:
<223> OTHER INFORMATION: DNA code

<400> SEQUENCE: 56
accacctaca aactgatcct gaacggcaag accctgacag gtgaaaccac caccatagct      60
gatgacgctg ctatggccga aaaagtgttg aaacagttcg ctttcgacaa tggtgtcgac     120
ggtgaatgga cctacgacgc cgctaccaaa accttcacgg ttaccgaa                  168

<210> SEQ ID NO 57
<211> LENGTH: 56
<212> TYPE: PRT
<213> ORGANISM: Artificial Sequence
<220> FEATURE:
<223> OTHER INFORMATION: SpG mutant

<400> SEQUENCE: 57

Thr Thr Tyr Lys Leu Ile Leu Asn Gly Lys Thr Leu Thr Gly Glu Thr
1               5                   10                  15

Thr Thr Ile Ala Val Asp Ala Ala Thr Ala Glu Ile Val Leu Lys Gln
            20                  25                  30

Tyr Ala Phe Asp Asn Gly Val Asp Gly Glu Trp Thr Tyr Asp Asp Ala
        35                  40                  45

Thr Lys Thr Phe Thr Val Thr Glu
    50                  55

<210> SEQ ID NO 58
<211> LENGTH: 168
<212> TYPE: DNA
<213> ORGANISM: Artificial Sequence
<220> FEATURE:
<223> OTHER INFORMATION: DNA code

<400> SEQUENCE: 58
accacctaca aactgatcct gaacggcaag accctgacag gtgaaaccac caccatagct      60
gttgacgctg ctaccgccga aatagtgctc aaacagtacg ctttcgacaa cggtgtcgac     120
ggtgaatgga cctacgacga cgctaccaaa accttcacgg ttaccgaa                  168

<210> SEQ ID NO 59
<211> LENGTH: 56
<212> TYPE: PRT
<213> ORGANISM: Artificial Sequence
<220> FEATURE:
<223> OTHER INFORMATION: SpG mutant

<400> SEQUENCE: 59

Thr Thr Tyr Lys Leu Ile Leu Asn Gly Lys Thr Leu Thr Gly Glu Thr
1               5                   10                  15

Thr Thr Ile Ala Val Asp Ala Ala Thr Ala Glu Ile Val Leu Lys Gln
            20                  25                  30

Phe Ala Asn Asp Asn Gly Val Asp Gly Gln Trp Thr Tyr Asp Tyr Ala
        35                  40                  45

Thr Lys Thr Phe Thr Val Thr Glu
    50                  55

<210> SEQ ID NO 60
<211> LENGTH: 168
<212> TYPE: DNA
<213> ORGANISM: Artificial Sequence
<220> FEATURE:
<223> OTHER INFORMATION: DNA code

<400> SEQUENCE: 60
accacctaca aactgatcct gaacggcaag accctgacag gtgaaaccac caccatagct      60
gttgacgctg ctaccgccga aatagtgctc aaacagttcg ctaacgacaa cggtgtcgac     120
ggtcaatgga cctacgacta tgctaccaaa accttcacgg ttaccgaa                  168

<210> SEQ ID NO 61
<211> LENGTH: 56
<212> TYPE: PRT
<213> ORGANISM: Artificial Sequence
<220> FEATURE:
<223> OTHER INFORMATION: SpG mutant

<400> SEQUENCE: 61

Thr Thr Tyr Lys Leu Ile Leu Asn Gly Lys Thr Leu Thr Gly Gln Thr
1               5                   10                  15

Thr Thr Val Ala Val Asp Ala Ala Thr Ala Glu Lys Val Leu Lys Gln
            20                  25                  30

Tyr Ala Asn Asp Asn Gly Leu Asp Gly Glu Trp Thr Tyr Asp Asp Ala
        35                  40                  45

Thr Lys Thr Phe Thr Val Thr Glu
    50                  55

<210> SEQ ID NO 62
<211> LENGTH: 168
<212> TYPE: DNA
<213> ORGANISM: Artificial Sequence
<220> FEATURE:
<223> OTHER INFORMATION: DNA code

<400> SEQUENCE: 62
accacctaca aactgatcct gaacggaaag accctgacag gtcagaccac caccgtagct     60
gttgacgctg ctacggccga aaaagtgctc aaacagtacg ctaatgacaa cggcctcgac    120
ggtgaatgga catacgacga cgctaccaaa accttcacgg ttaccgaa                 168

<210> SEQ ID NO 63
<211> LENGTH: 56
<212> TYPE: PRT
<213> ORGANISM: Artificial Sequence
<220> FEATURE:
<223> OTHER INFORMATION: SpG mutant

<400> SEQUENCE: 63

Thr Thr Tyr Lys Leu Ile Leu Asn Gly Lys Thr Leu Thr Gly Thr Thr
1               5                   10                  15

Thr Thr Ile Ala Val Asp Ala Ala Met Ala Gly Lys Val Leu Lys Gln
            20                  25                  30

Tyr Ala Tyr Asp Asn Gly Val Asp Gly Glu Trp Thr Tyr Asp Asp Ala
        35                  40                  45

Thr Lys Thr Phe Thr Val Thr Glu
    50                  55

<210> SEQ ID NO 64
<211> LENGTH: 168
<212> TYPE: DNA
<213> ORGANISM: Artificial Sequence
<220> FEATURE:
<223> OTHER INFORMATION: DNA code

<400> SEQUENCE: 64
accacctaca aactaatcct gaacggcaag accctgacag gtacaaccac caccatagct     60
gtagacgctg ctatggctgg aaaagtgctc aaacagtacg cttacgacaa cggagtcgac    120
ggtgaatgga cctacgacga cgctaccaaa accttcacgg ttaccgaa                 168

<210> SEQ ID NO 65
<211> LENGTH: 56
<212> TYPE: PRT
<213> ORGANISM: Artificial Sequence
<220> FEATURE:
<223> OTHER INFORMATION: SpG mutant

<400> SEQUENCE: 65

Thr Thr Tyr Lys Leu Ile Leu Asn Gly Lys Thr Leu Thr Gly Glu Thr
1               5                   10                  15

Thr Thr Ile Ala Val Asp Ala Ala Thr Ala Glu Lys Val Leu Lys Gln
                20                  25                  30

Tyr Ala Asn Asp Asn Gly Val Asp Gly Glu Trp Thr Tyr Asp Ala Ala
            35                  40                  45

Thr Glu Thr Phe Thr Val Thr Glu
    50                  55

<210> SEQ ID NO 66
<211> LENGTH: 168
<212> TYPE: DNA
<213> ORGANISM: Artificial Sequence
<220> FEATURE:
<223> OTHER INFORMATION: DNA code

<400> SEQUENCE: 66
accacctaca aactgatcct gaacggcaag accctgacag gtgaaaccac caccatagca     60
gttgacgctg ctacggccga aaaagtgctc aaacagtacg caaacgacaa cggtgtcgac    120
ggtgaatgga cctacgatgc cgctaccgaa accttcacgg ttaccgaa                 168

<210> SEQ ID NO 67
<211> LENGTH: 56
<212> TYPE: PRT
<213> ORGANISM: Artificial Sequence
<220> FEATURE:
<223> OTHER INFORMATION: SpG mutant

<400> SEQUENCE: 67

Thr Thr Tyr Lys Leu Ile Leu Asn Gly Lys Thr Leu Thr Gly Glu Thr
1               5                   10                  15

Thr Ala Val Ala Val Asp Ala Ala Thr Ala Glu Lys Val Leu Lys Gln
                20                  25                  30

Phe Ala Asn Asp Asn Gly Val Asp Gly Glu Trp Thr Tyr Asp Asp Ala
            35                  40                  45

Thr Lys Thr Phe Thr Val Thr Glu
    50                  55

<210> SEQ ID NO 68
<211> LENGTH: 168
<212> TYPE: DNA
<213> ORGANISM: Artificial Sequence
<220> FEATURE:
<223> OTHER INFORMATION: DNA code

<400> SEQUENCE: 68
accacctaca aactgatcct gaacggcaag accctgacag gtgaaaccac cgccgtagct     60
gttgacgctg ctacggccga aaaagtgctc aaacagttcg ctaacgacaa cggtgtcgac    120
ggtgaatgga cctacgacga tgctaccaaa accttcacgg ttaccgaa                 168

<210> SEQ ID NO 69
<211> LENGTH: 56
<212> TYPE: PRT
<213> ORGANISM: Artificial Sequence
<220> FEATURE:
<223> OTHER INFORMATION: SpG mutant

<400> SEQUENCE: 69

Thr Thr Tyr Lys Leu Ile Leu Asn Gly Arg Thr Leu Thr Gly Gln Thr
1               5                   10                  15

Thr Thr Glu Ala Val Asp Ala Ala Thr Ala Glu Arg Val Leu Lys Gln
            20                  25                  30

Tyr Ala Asn Gly Asn Gly Val Asp Gly Val Trp Thr Tyr Asp Asp Ala
        35                  40                  45

Thr Lys Thr Phe Thr Val Thr Glu
    50                  55

<210> SEQ ID NO 70
<211> LENGTH: 168
<212> TYPE: DNA
<213> ORGANISM: Artificial Sequence
<220> FEATURE:
<223> OTHER INFORMATION: DNA code

<400> SEQUENCE: 70
accacctaca aactgatcct gaacggcagg accctgacag gtcaaaccac caccgaagct     60
gttgacgctg ctacggccga aagagtgctc aaacagtacg ctaacggcaa cggtgtcgac    120
ggtgtatgga catacgacga tgctaccaaa accttcacgg ttaccgaa                 168

<210> SEQ ID NO 71
<211> LENGTH: 56
<212> TYPE: PRT
<213> ORGANISM: Artificial Sequence
<220> FEATURE:
<223> OTHER INFORMATION: SpG mutant

<400> SEQUENCE: 71

Thr Thr Tyr Lys Leu Ile Leu Asn Gly Lys Thr Leu Thr Gly Glu Thr
1               5                   10                  15

Thr Thr Glu Ala Val Asp Ala Ala Thr Ala Glu Ile Val Leu Lys Gln
            20                  25                  30

Tyr Ala Asn Gly Asn Gly Ile Asp Gly Glu Trp Thr Tyr Asp Asp Ala
        35                  40                  45

Thr Lys Thr Phe Thr Val Thr Glu
    50                  55

<210> SEQ ID NO 72
<211> LENGTH: 168
<212> TYPE: DNA
<213> ORGANISM: Artificial Sequence
<220> FEATURE:
<223> OTHER INFORMATION: DNA code

<400> SEQUENCE: 72
accacctaca aactgatcct gaacggaaag accctgacag gtgaaaccac caccgaagct     60
gttgacgctg ctaccgccga aatagtgctc aaacagtacg ctaacggcaa cggtatcgac    120
ggtgaatgga cctacgacga cgctaccaaa accttcacgg ttaccgaa                 168

<210> SEQ ID NO 73
<211> LENGTH: 56
<212> TYPE: PRT
<213> ORGANISM: Artificial Sequence
<220> FEATURE:
<223> OTHER INFORMATION: SpG mutant

<400> SEQUENCE: 73

Thr Thr Tyr Lys Leu Ile Leu Asn Gly Lys Thr Leu Thr Gly Glu Thr
1               5                   10                  15

Thr Thr Glu Ala Val Asn Thr Ala Ser Ala Glu Lys Val Leu Lys Gln
            20                  25                  30

Tyr Ala Asn Asp Asn Gly Val Asp Gly Glu Trp Thr Tyr Asp Asp Thr
        35                  40                  45

Thr Lys Thr Phe Thr Val Thr Glu
    50                  55

<210> SEQ ID NO 74
<211> LENGTH: 168
<212> TYPE: DNA
<213> ORGANISM: Artificial Sequence
<220> FEATURE:
<223> OTHER INFORMATION: DNA code

<400> SEQUENCE: 74
accacctaca aactgatcct gaacggaaag accctgacag agaaaccac caccgaagct      60 gttaacactg cttcggccga aaaagtgctc aaacagtacg ctaacgacaa cggtgtcgac     120
ggcgaatgga cctacgacga cactaccaaa accttcacgg ttaccgaa                  168

<210> SEQ ID NO 75
<211> LENGTH: 56
<212> TYPE: PRT
<213> ORGANISM: Artificial Sequence
<220> FEATURE:
<223> OTHER INFORMATION: SpG mutant

<400> SEQUENCE: 75

Thr Thr Tyr Lys Leu Ile Leu Asn Gly Lys Thr Leu Thr Gly Glu Thr
1               5                   10                  15

Thr Thr Ile Ala Asp Asp Ala Ala Thr Ala Glu Ile Val Leu Arg Gln
            20                  25                  30

Tyr Ala Asn Asp Asn Gly Val Asp Gly Glu Trp Thr Tyr Asp His Ala
        35                  40                  45

Thr Lys Thr Phe Thr Val Thr Glu
    50                  55

<210> SEQ ID NO 76
<211> LENGTH: 168
<212> TYPE: DNA
<213> ORGANISM: Artificial Sequence
<220> FEATURE:
<223> OTHER INFORMATION: DNA code

<400> SEQUENCE: 76
accacctaca aactgatcct gaacggcaag accctgacag gtgaaaccac caccatagct      60
gatgacgctg ctactgccga gatagtgctc agacagtacg ctaacgacaa cggagtcgac     120
ggtgaatgga cctacgacca cgctaccaaa accttcacgg ttaccgaa                  168

<210> SEQ ID NO 77
<211> LENGTH: 56
<212> TYPE: PRT
<213> ORGANISM: Artificial Sequence
<220> FEATURE:
<223> OTHER INFORMATION: SpG mutant

<400> SEQUENCE: 77

Thr Thr Tyr Lys Leu Ile Leu Asn Gly Lys Thr Leu Thr Gly Gln Thr
1               5                   10                  15

Thr Thr Ile Ala Val Asp Ala Ala Thr Ala Asp Lys Val Phe Lys Gln
            20                  25                  30

Tyr Ala Asn Asp Asn Gly Ile Asp Gly Glu Trp Thr Tyr Asp His Ala
        35                  40                  45

Thr Lys Thr Phe Thr Val Thr Glu
    50                  55

<210> SEQ ID NO 78
<211> LENGTH: 168
<212> TYPE: DNA
<213> ORGANISM: Artificial Sequence
<220> FEATURE:
<223> OTHER INFORMATION: DNA code

<400> SEQUENCE: 78
accacctaca aactgatcct gaacgggaag accctgacag gtcaaaccac caccatagct      60
gttgacgctg ctacggccga taaagtgttc aaacagtacg ctaacgacaa cggtatcgac     120
ggcgaatgga cctacgacca cgctaccaaa accttcacgg ttaccgaa                  168

<210> SEQ ID NO 79
<211> LENGTH: 56
<212> TYPE: PRT
<213> ORGANISM: Artificial Sequence
<220> FEATURE:
<223> OTHER INFORMATION: SpG mutant

<400> SEQUENCE: 79

Thr Thr Tyr Lys Leu Ile Leu Asn Gly Lys Thr Leu Thr Gly Glu Thr
1               5                   10                  15

Thr Thr Ile Ala Val Glu Ala Thr Thr Ala Glu Lys Val Leu Lys Gln
            20                  25                  30

Phe Ala Asn Asp Asn Gly Val Asp Gly Glu Trp Thr Tyr Asp Gly Ala
        35                  40                  45

Thr Lys Thr Phe Thr Val Thr Glu
    50                  55

<210> SEQ ID NO 80
<211> LENGTH: 168
<212> TYPE: DNA
<213> ORGANISM: Artificial Sequence
<220> FEATURE:
<223> OTHER INFORMATION: DNA code

<400> SEQUENCE: 80
accacctaca aactgatcct gaacgggaag accctgacag gtgaaaccac caccatagct      60
gttgaagcta ctacggccga aaaagtgctc aaacagttcg ctaacgacaa cggtgtcgac     120
ggcgaatgga cctacgacgg tgctaccaaa accttcacgg ttaccgaa                  168

<210> SEQ ID NO 81
<211> LENGTH: 56
<212> TYPE: PRT
<213> ORGANISM: Artificial Sequence
<220> FEATURE:
<223> OTHER INFORMATION: SpG mutant

<400> SEQUENCE: 81

Thr Thr Tyr Lys Leu Ile Leu Asn Gly Lys Thr Leu Ser Gly Glu Thr
1               5                   10                  15

Thr Thr Val Ala Val Asp Ala Ala Thr Ala Glu Lys Val Leu Lys Gln
            20                  25                  30

Phe Ala Asn Asp Asn Gly Val Asp Gly Glu Trp Thr Tyr Asp Asp Ala
        35                  40                  45

Thr Lys Thr Phe Thr Val Thr Glu
    50                  55

<210> SEQ ID NO 82
<211> LENGTH: 168
<212> TYPE: DNA
<213> ORGANISM: Artificial Sequence
<220> FEATURE:
<223> OTHER INFORMATION: DNA code

<400> SEQUENCE: 82
accacctaca aactgatcct gaacggcaag accctatcag gtgaaaccac aaccgtagct    60
gttgacgcag ctacggccga aaagttctc aaacagttcg ctaacgacaa cggtgtcgat    120
ggtgaatgga cctacgacga cgctaccaaa accttcacgg ttaccgaa                168

<210> SEQ ID NO 83
<211> LENGTH: 56
<212> TYPE: PRT
<213> ORGANISM: Artificial Sequence
<220> FEATURE:
<223> OTHER INFORMATION: SpG mutant

<400> SEQUENCE: 83

Thr Thr Tyr Lys Leu Ile Leu Asn Gly Lys Thr Leu Thr Gly Glu Thr
1               5                   10                  15

Thr Thr Ile Ala Val Asp Ala Ala Thr Ala Glu Lys Val Leu Lys Gln
            20                  25                  30

Tyr Ala Asn Asp Asn Gly Val Asp Gly Glu Trp Thr Phe Asp Tyr Ala
        35                  40                  45

Thr Lys Thr Phe Thr Val Thr Glu
    50                  55

<210> SEQ ID NO 84
<211> LENGTH: 168
<212> TYPE: DNA
<213> ORGANISM: Artificial Sequence
<220> FEATURE:
<223> OTHER INFORMATION: DNA code

<400> SEQUENCE: 84
accacctaca aactgatcct gaacggcaag accctgacag gtgaaaccac caccatagct    60
gttgacgctg ctacggccga aaagtgctc aaacaatacg ctaacgacaa cggtgtcgac    120
ggcgaatgga ccttcgacta cgctaccaaa accttcacgg ttaccgaa                168

<210> SEQ ID NO 85
<211> LENGTH: 56
<212> TYPE: PRT
<213> ORGANISM: Artificial Sequence
<220> FEATURE:
<223> OTHER INFORMATION: SpG mutant

```
<400> SEQUENCE: 85

Thr Thr Tyr Lys Leu Ile Leu Asn Gly Lys Thr Leu Thr Gly Glu Thr
1               5                   10                  15

Thr Ala Ile Ala Ala Asp Ala Ala Thr Ala Glu Ile Val Leu Lys Gln
            20                  25                  30

Phe Ala Asn Asp Asn Gly Ile Asp Gly Glu Trp Thr Tyr Asp Asp Ala
        35                  40                  45

Thr Lys Thr Phe Thr Val Thr Glu
    50                  55

<210> SEQ ID NO 86
<211> LENGTH: 168
<212> TYPE: DNA
<213> ORGANISM: Artificial Sequence
<220> FEATURE:
<223> OTHER INFORMATION: DNA code

<400> SEQUENCE: 86
accacctaca aactgatcct gaacggcaag accctgacag gtgaaaccac cgccatcgct      60
gctgacgctg ctacggccga aattgtgctc aaacagttcg ctaacgacaa cggtatcgac     120
ggtgaatgga cctacgacga cgctaccaaa accttcacgg ttaccgaa                  168

<210> SEQ ID NO 87
<211> LENGTH: 56
<212> TYPE: PRT
<213> ORGANISM: Artificial Sequence
<220> FEATURE:
<223> OTHER INFORMATION: SpG mutant

<400> SEQUENCE: 87

Thr Thr Tyr Lys Leu Ile Leu Asn Gly Arg Thr Leu Thr Gly Glu Thr
1               5                   10                  15

Thr Ala Ile Ala Asp Asp Ala Ala Met Ala Glu Lys Val Leu Lys Gln
            20                  25                  30

Phe Ala Phe Asp Asn Gly Val Asp Gly Glu Trp Thr Tyr Asp Ala Ala
        35                  40                  45

Thr Lys Thr Phe Thr Val Thr Glu
    50                  55

<210> SEQ ID NO 88
<211> LENGTH: 168
<212> TYPE: DNA
<213> ORGANISM: Artificial Sequence
<220> FEATURE:
<223> OTHER INFORMATION: DNA code

<400> SEQUENCE: 88
accacctaca aactgatcct gaacggcagg accctgactg gtgaaaccac cgccatagct      60
gatgacgctg ctatggccga aaaagtgttg aaacagttcg ctttcgacaa tggcgtcgac     120
ggtgaatgga cctacgatgc cgctaccaaa accttcacgg ttaccgaa                  168
```